US010532058B2

(12) United States Patent
Fischer et al.

(10) Patent No.: US 10,532,058 B2
(45) Date of Patent: Jan. 14, 2020

(54) PROCESS FOR PREPARING CEFTOLOZANE FROM 7-AMINOCEPHALOSPORANIC ACID (7-ACA)

(71) Applicant: Sandoz AG, Basel (CH)

(72) Inventors: Michael Fischer, Kundl (AT); Wolfgang Felzmann, Kundl (AT); Ronny Huetz, Kundl (AT); Martin Langner, Kundl (AT); Birgit Endl, Kundl (AT)

(73) Assignee: Sandoz AG, Basel (CH)

(*) Notice: Subject to any disclaimer, the term of this patent is extended or adjusted under 35 U.S.C. 154(b) by 0 days.

(21) Appl. No.: 15/756,214

(22) PCT Filed: Sep. 7, 2016

(86) PCT No.: PCT/EP2016/071021
§ 371 (c)(1),
(2) Date: Feb. 28, 2018

(87) PCT Pub. No.: WO2017/042188
PCT Pub. Date: Mar. 16, 2017

(65) Prior Publication Data
US 2018/0338981 A1 Nov. 29, 2018

(30) Foreign Application Priority Data
Sep. 8, 2015 (EP) .................... 15184317

(51) Int. Cl.
C07D 501/56 (2006.01)
C07D 501/14 (2006.01)
C07D 285/08 (2006.01)
A61K 31/545 (2006.01)
C07D 501/60 (2006.01)
C07D 501/04 (2006.01)
A61P 31/04 (2006.01)
C07D 501/16 (2006.01)

(52) U.S. Cl.
CPC ............ A61K 31/545 (2013.01); A61P 31/04 (2018.01); C07D 285/08 (2013.01); C07D 501/04 (2013.01); C07D 501/14 (2013.01); C07D 501/56 (2013.01); C07D 501/60 (2013.01)

(58) Field of Classification Search
CPC ... C07D 501/06; C07D 501/12; C07D 501/56
See application file for complete search history.

(56) References Cited

FOREIGN PATENT DOCUMENTS

| CN | 102040615 A | 5/2011 |
|---|---|---|
| JP | 01308288 | 12/1989 |
| JP | 07101960 | 4/1995 |
| WO | 02090364 A1 | 11/2002 |
| WO | 2004039814 A1 | 5/2004 |
| WO | 2014152763 A1 | 9/2015 |
| WO | 2016025839 A1 | 2/2016 |

OTHER PUBLICATIONS

International Search Report and Written Opinion for PCT/EP2016/071021, dated Oct. 21, 2016, 13 pages.
Toda, Ayako, et al., Synthesis and SAR of novel parenteral anti-pseudomonal cephalosporins: Discovery of FR264205, Bioorganic and Medicinal Chemistry Letters, vol. 18, 2008, pp. 4849-4852.
Preliminary Report on Patentability for PCT/EP2016/071021, dated Mar. 22, 2018, 9 pages.

Primary Examiner — Emily A Bernhardt
(74) Attorney, Agent, or Firm — Luedeka Neely Group, P.C.

(57) ABSTRACT

The present invention relates to a highly convergent method for the synthesis and purification of ceftolozane and intermediates starting from 7-aminocephaiosporanic acid (7-ACA).

14 Claims, No Drawings

PROCESS FOR PREPARING CEFTOLOZANE FROM 7-AMINOCEPHALOSPORANIC ACID (7-ACA)

This application is a Section 371 national phase entry of PCT application PCT/EP2016/071021, filed Sep. 7, 2016. This application also claims the benefit of the earlier filing date of European patent application 15184317.4, filed Sep. 8, 2015.

The present invention relates to a highly convergent method for the synthesis and purification of ceftolozane and intermediates starting from 7-aminocephalosporanic acid (7-ACA).

Ceftolozane (FR264205) is an antibacterial agent, belonging to the family of cephalosporin antibiotics. It is also referred to as a cephem antibiotic. The FDA approved ceftolozane in combination with tazobactam for the treatment of urinary tract and intra-abdominal infections in 2014. In the marketed product ceftolozane sulfate is contained, which is depicted below:

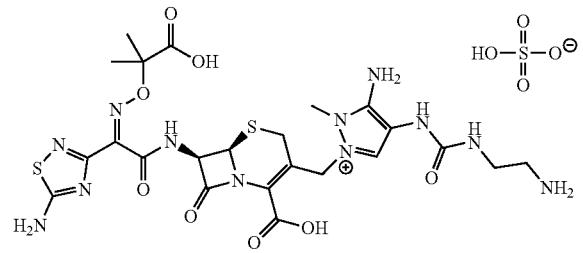 [SMILES: Cn1c(N)c(NC(=O)NCCN)c[n+]1CC1=C(C(=O)O)N2C(=O)[C@@H](NC(=O)/C(=N\OC(C)(C)C(=O)O)c3nsc(N)n3)[C@H]2SC1 ; O=S(=O)([O-])O]

Two processes for the production of cephem compounds are disclosed in WO 2004/039814. In the first approach, the cephem core structure is reacted first with the thiadiazole moiety (7-side chain) and subsequently the pyrazole moiety is introduced. The second approach relates to the reversed sequence wherein the cephem core structure is first reacted with the pyrazole moiety and subsequently the thiadiazole moiety is introduced. In all examples of the experimental section of WO 2004/039814 the first strategy is used.

Preparation 1 and 2 and example 1 of WO 2004/039814 thus disclose a synthesis of ceftolozane, using a benzhydryl protected cephalosporine derivative as cephem core structure. The 7-side chain is activated as an acyl chloride and coupled with the amino functionality of the cephem core after Boc protection. The final assembly of ceftolozane, the introduction of the substituted pyrazole moiety and the global deprotection is accomplished in low yield (~5%, for purification see below):

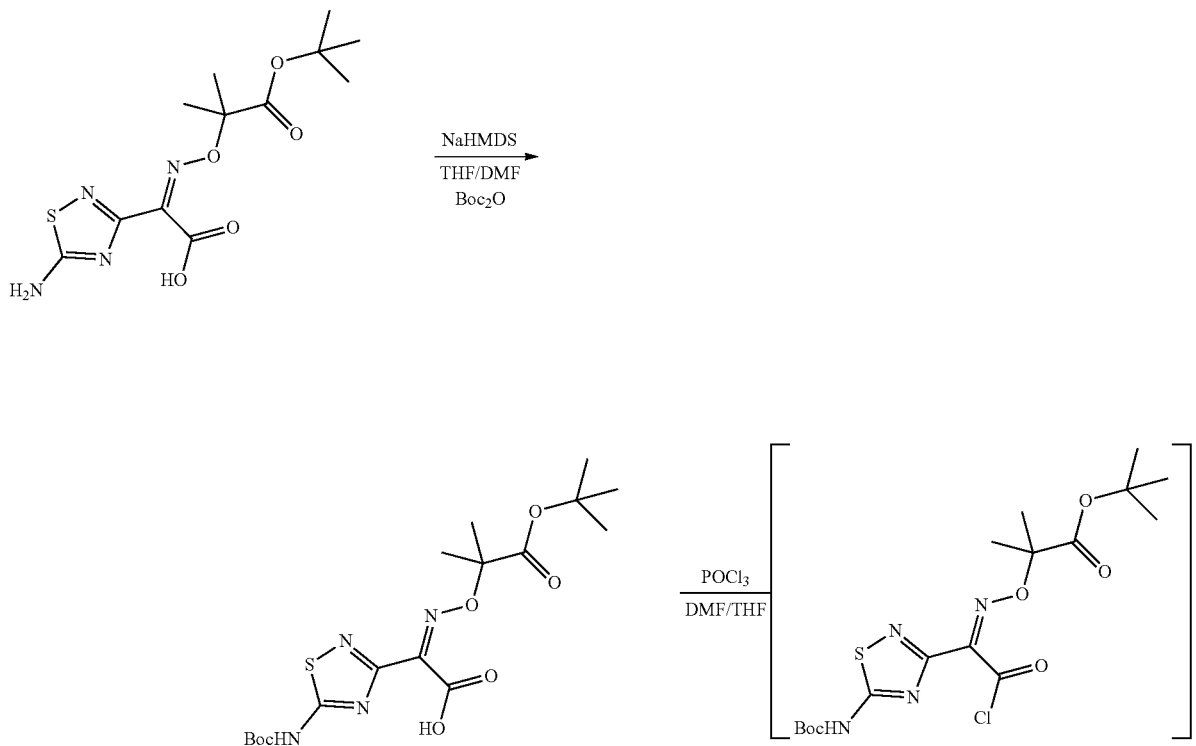

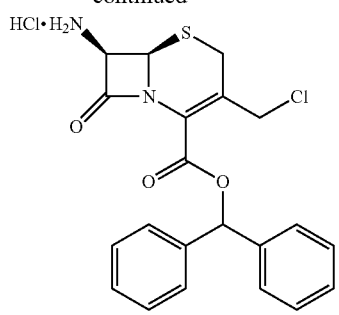
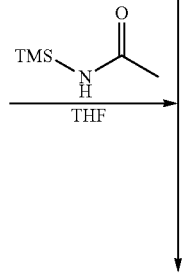

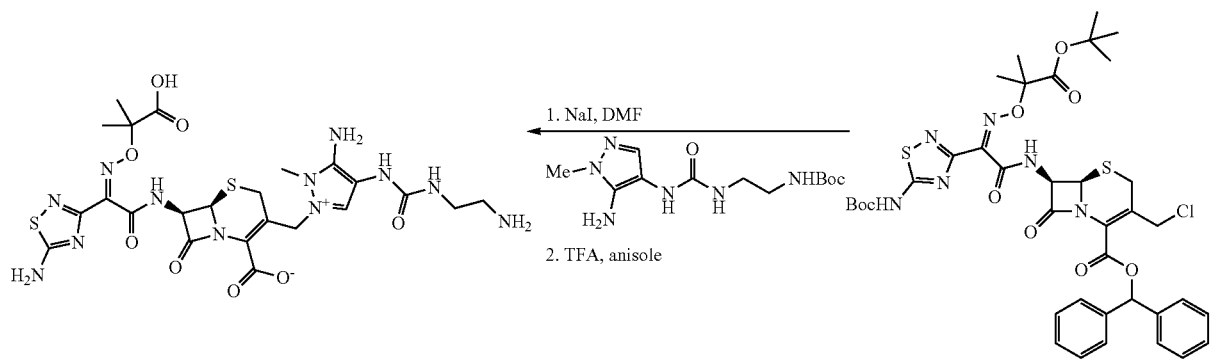

In preparation 7 and example 2 of WO 2004/039814, also the pyrazole side chain is coupled to the cephem core which already carries the thiadiazole moiety. Here, a trityl protected version of the pyrazole side chain is used and the amino functionality of the thiadiazole moiety of the cephalosporine derivative was protected with a trimethylsilyl group prior to the pyrazole coupling. Global deprotection furnished ceftolozane in low yield (for purification see below):

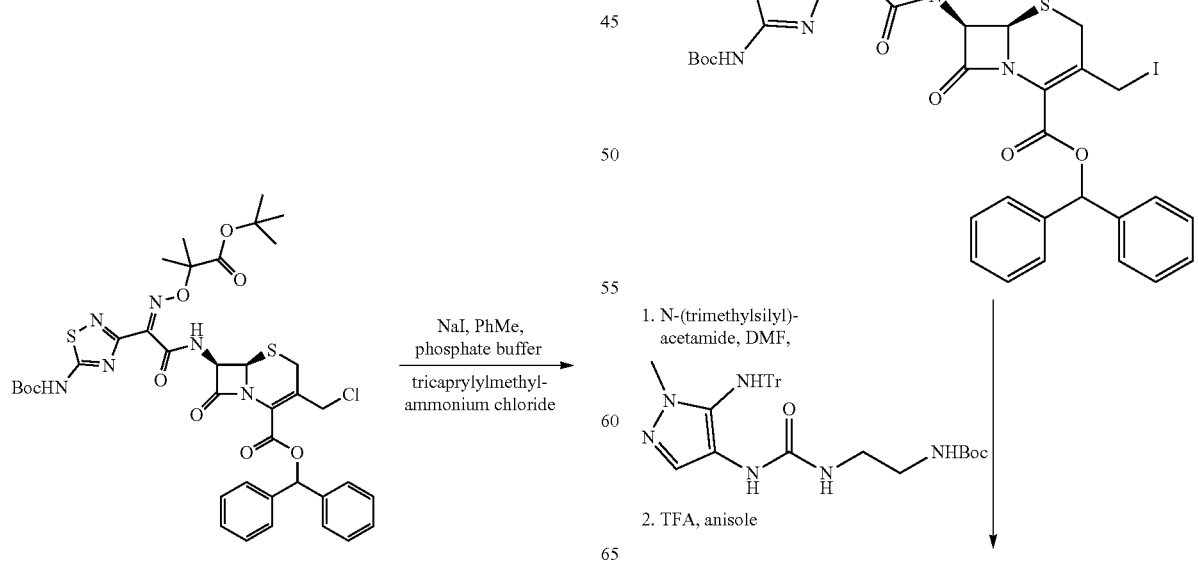

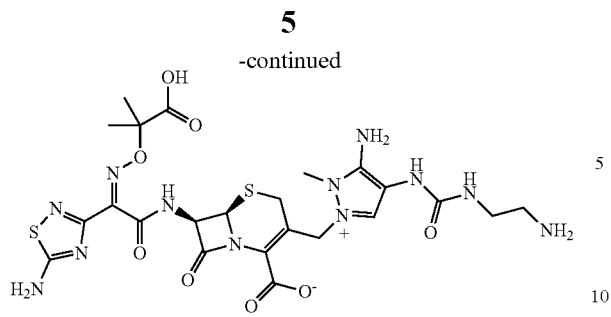

The purification of crude ceftolozane to produce ceftolozane sulfate is also described in example 7 of WO 2004/039814:

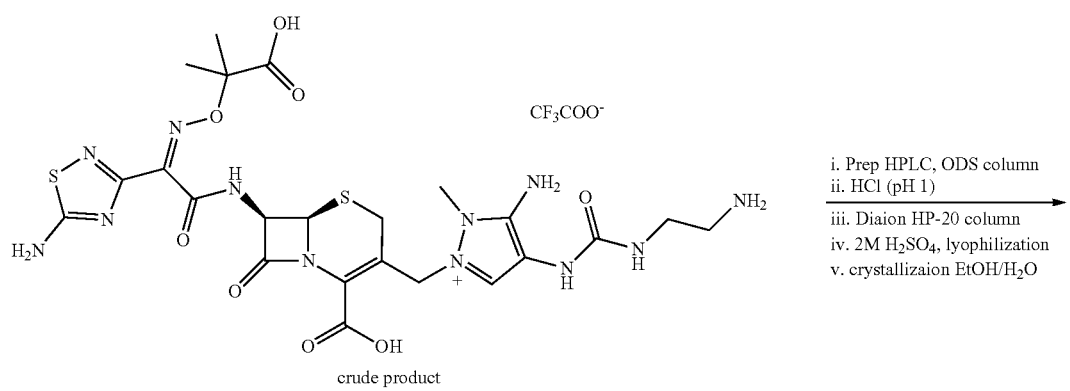

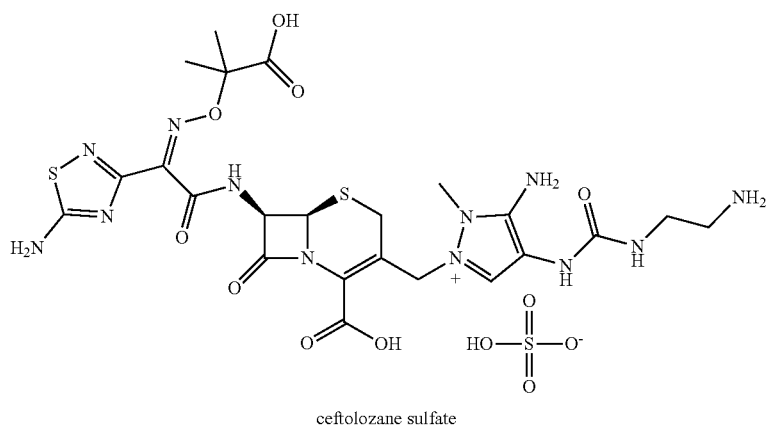

In an alternative synthesis of WO 2004/039814 (preparation 48) the 7-side chain was activated as a mixed anhydride in situ and subsequently coupled with a para-methoxybenzyl (PMB) protected cephalosporin derivative (GCL). The thiadiazole moiety was then trimethylsilyl (TMS) protected with 1,3-bis(trimethylsilyl)urea (BSU) and the pyrazole side chain was introduced via its trityl protected version (see above) (example 26 of WO 2004/039814). Ceftolozane sulfate was obtained in low yield after extensive purification steps. The same overall reaction sequence, starting from GCL, is also depicted in Scheme 2 of *Bioorg. Med. Chem. Lett.* 2008, 18, 4849 with higher yields are indicated, but no experimental details are given:

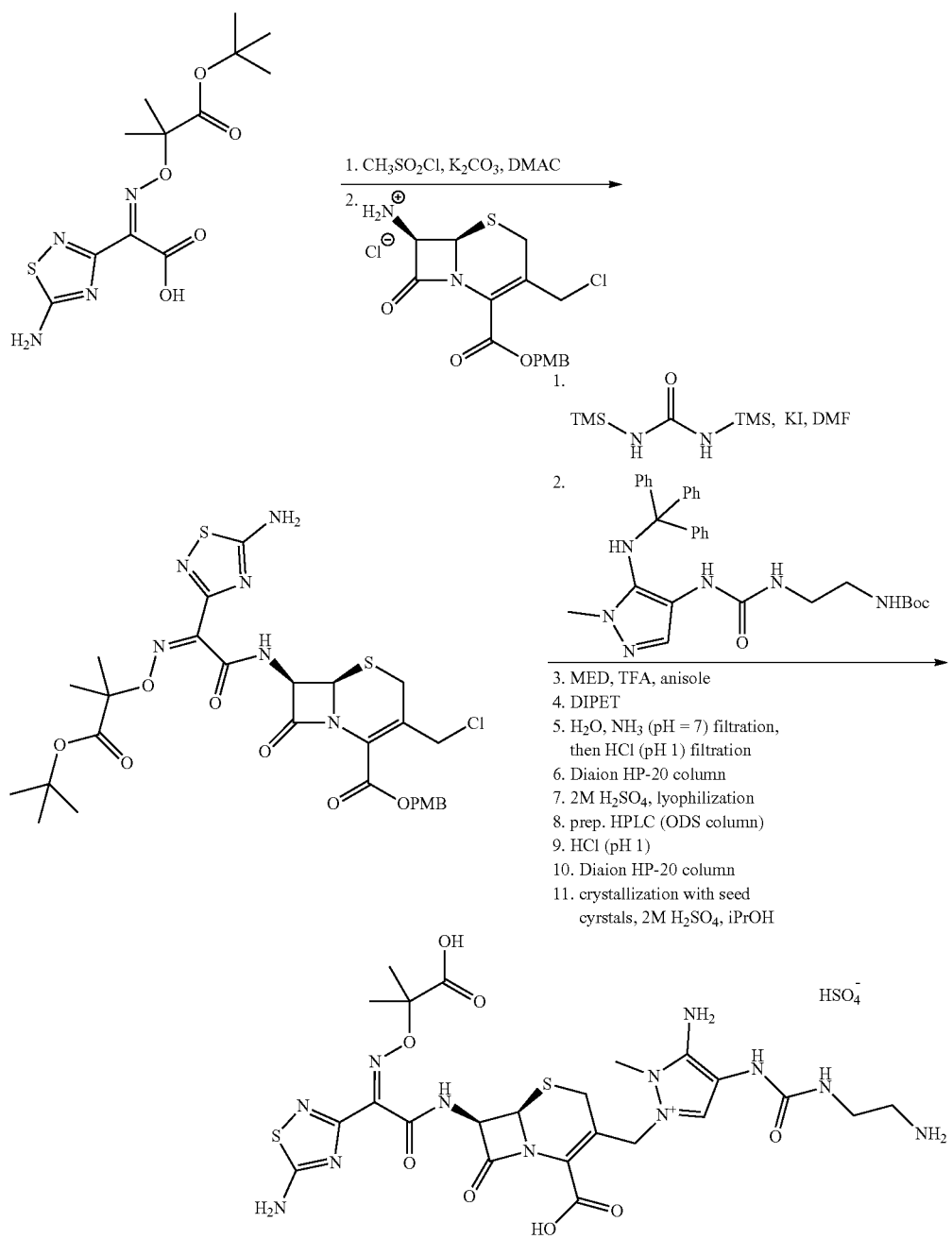

All exemplified methods of synthesis in WO 2004/039814 thus relied on the coupling of the pyrazole moiety to the cephem core already carrying the thiadiazole moiety. The obtained yields are low and extensive purification steps (2× Diaion HP-20 column, preparative RP-HPLC, precipitation, 2 filtrations) were necessary for all described preparations of ceftolozane sulfate, limiting the applicability of these approaches for industrial scale product ion.

In contrast to all examples of WO 2004/039814, in WO 2014/152763 ceftolozane is assembled by coup ling first the pyrazole side chain to the PMB protected cephem core structure followed by coupling of the 7-side chain. A synthesis of ceftolozane is disclosed using a salicylaldehyde imine cephalosporine derivative as starting material. The pyrazole side chain was introduced via its trityl protected version. Subsequently the 7-side chain was activated as a methanesulfonic anhydride and coupled with the salicylaldehyde imine pyrazole intermediate. Global deprotection using trifluoroacetic acid and anisole and purification furnished the ceftolozane TFA salt and the anion was then changed furnishing ceftolozane sulfate. For purification a RP-HPLC was necessary in WO 2014/152763, limiting the applicability of this approach for a production on industrial scale. Furthermore, no yield was indicated for the last step in WO 2014/152763. A repetition of WO 2014/152763 gave a yield for the 7-side chain coupling that was considerably lower compared to what is indicated in WO 2014/152763 and the yield for the global deprotection step (which was not indicated in WO 2014/152763) was very low (~15%) (see comparative example for the yields obtained upon repetition; the synthesis scheme of WO 2014/152763 is also depicted there).

An improved method of preparation of ceftolozane is thus desirable. A major challenge in this respect is the purification of intermediates and the active pharmaceutical ingredient (API). Preferably, the method should be efficient in terms of material costs and purifications steps needed.

It was surprisingly found by the inventors of the present invention, that ceftolozane can be prepared in good yield in a process which comprises relatively few purification steps for intermediates and the final product. The process can thus easily be scaled up to an industrial process. The process was possible by a reaction scheme using 7-aminocephalosporanic acid (7-ACA) as the starting material, which is silylated and activated with, e.g., iodo(trimethyl)silane (TMJS). The pyrazole moiety, after optionally reacting it with a silylating agent, is introduced by nucleophilic displacement of the iodide. Subsequently, the thiadiazole moiety is coupled with the amino functionality of the cephem core already carrying the pyrazole moiety. The sequence (alkylation & amide coupling) can be done in a one-pot procedure without isolation of the intermediate after alkylation. Using an orthogonal protecting group strategy for the amino functionality of the pyrazole moiety (i.e. choosing amino protecting groups for R1 and/or R2 which can be selectively removed under conditions not affecting R3, R4, R7 and R10, see below), the selective cleavage of R1 and R2 furnishes an intermediate which can be isolated after removal of insoluble impurities. Further, if the amino functionality of the pyrazole moiety is protected by triphenylmethyl (i.e. if R1 or R2 is trityl, see below), the selective cleavage of the triphenylmethyl (trityl) protecting group furnishes an amorphous intermediate after removal of insoluble impurities, which can be reslurried to give a crystalline final intermediate. The isolation of said intermediate can be advantageous because it allows, for example, for impurities to be advantageously removed in form of a precipitate that is filtered off. After global deprotection ceftolozane is obtained as amorphous solid, which can be recrystallized for further purification. By using this sequence ceftolozane can be rapidly synthesized in a convergent manner in three or four steps. Compared to previous synthesis the novel approach is more efficient being comparable or even shorter regarding the number of synthetic steps and using a cheaper starting material (7-ACA).

The synthesis sequence of the present invention is shown in an exemplary manner below:

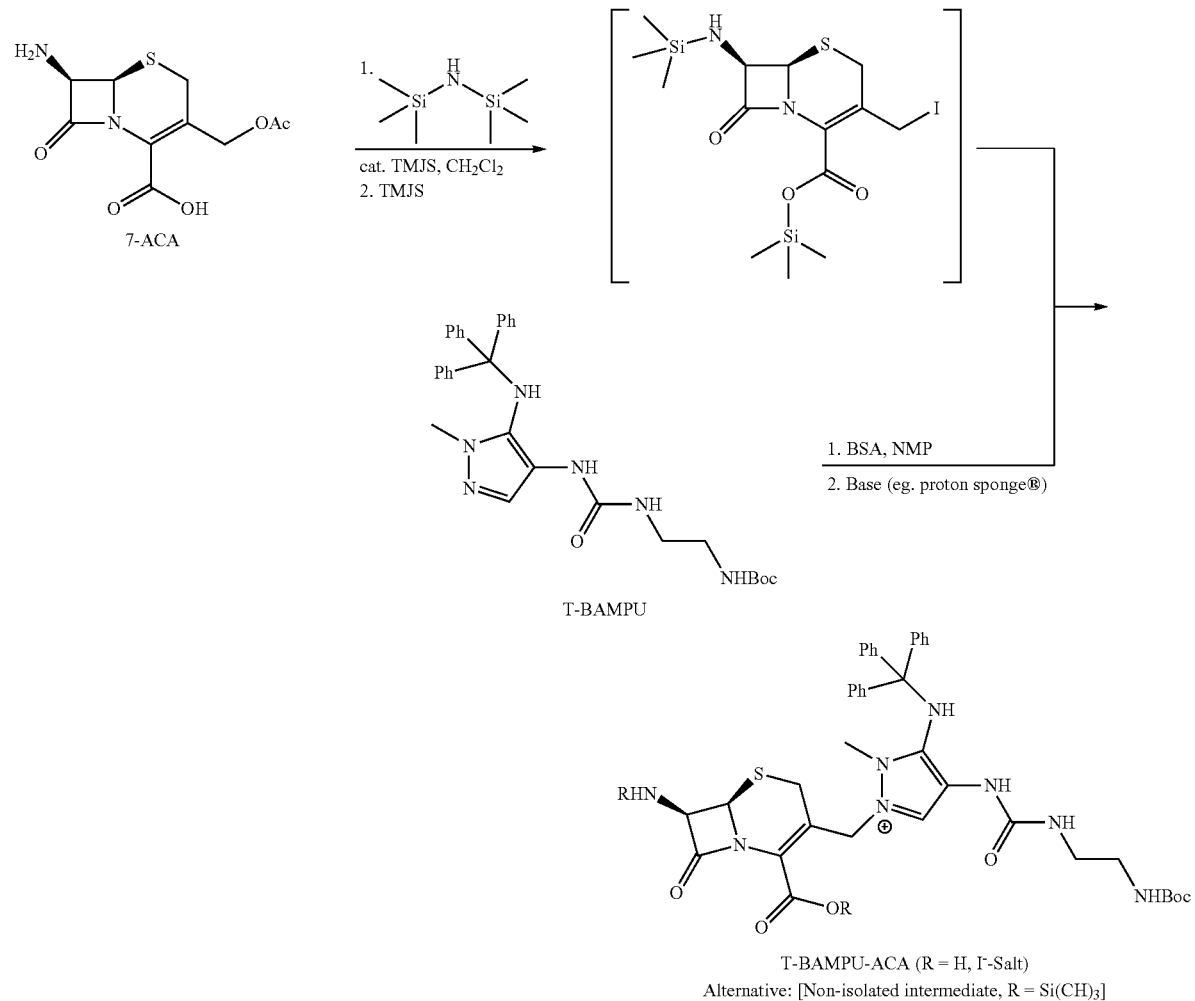

T-BAMPU-ACA (R = H, I⁻-Salt)
Alternative: [Non-isolated intermediate, R = Si(CH₃)₃]

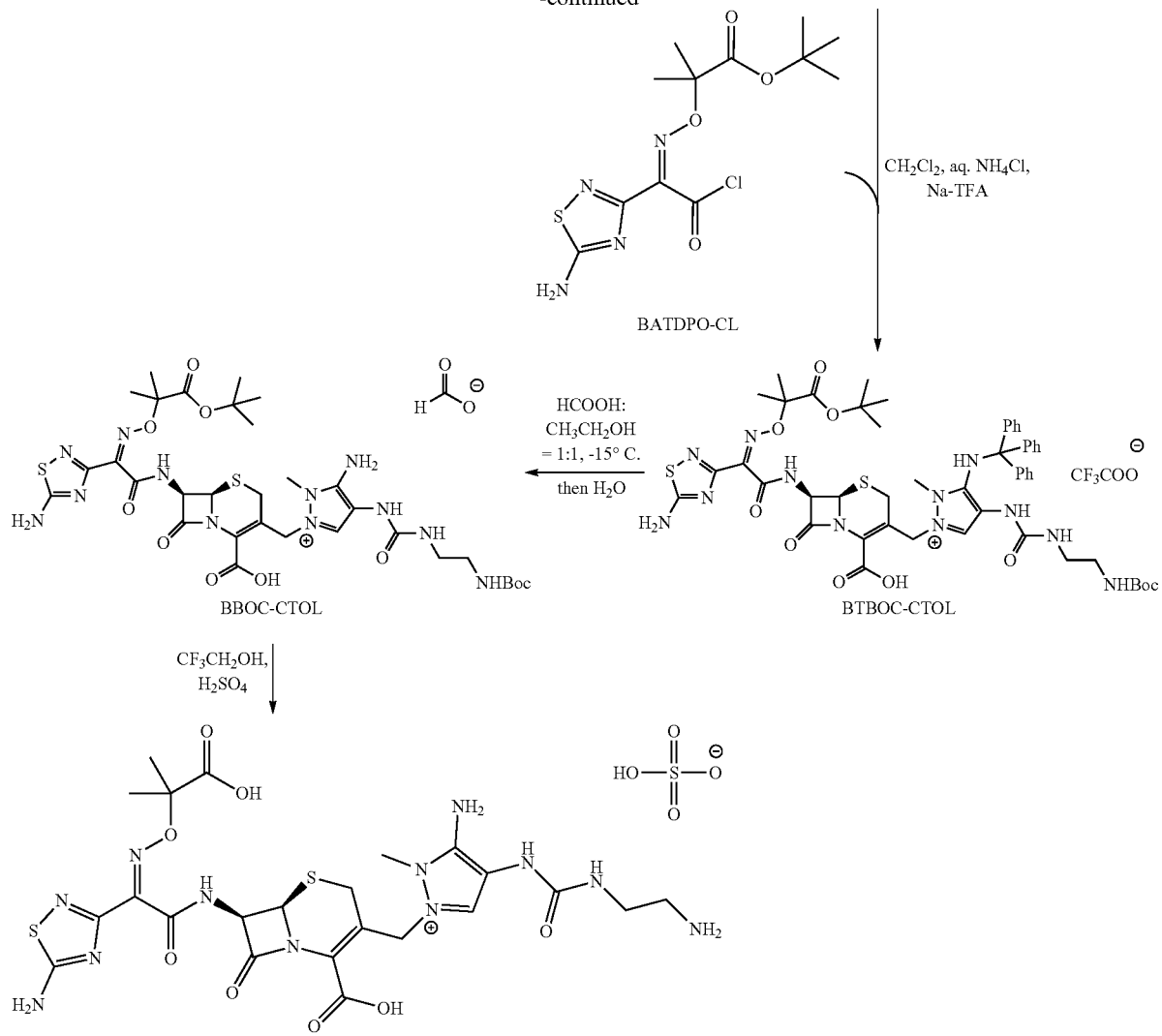

Compared to WO 2014/152763, in particular a different and cheaper starting material is used, which is available on bulk scale (7-ACA instead of a PMB-protected salicylaldehyde imine cephalosporine derivative). It was further found that the thiadiazole moiety can be introduced as acyl chloride or thioester instead of a mixed anhydride (methanesulfonic anhydride). Protection of the amino group of the thiadiazole moiety is not necessary in the process of the present invention. The process for production of ceftolozane can be conducted more efficiently with lower raw-material costs, less solvents, and RP-HPLC purification is not necessarily required for purification. With a selective deprotecting strategy, using a triphenylmethyl-protecting group as residues $R_1$ or $R_2$ and using protecting groups as residues $R_3$, $R_4$, $R_7$ and $R_{10}$ which are not removed when triphenylmethyl-protecting groups are removed, it was found that an intermediate can be obtained which can easily be purified. In this intermediate impurities can advantageously be removed in form of a precipitate that is filtered off. Of course, it is also possible that one or more of $R_3$, $R_4$, $R_7$ and $R_{10}$ are also triphenylmethyl. In such a case, these residues will also be removed when removing $R_1$ and $R_2$, and the corresponding residues in the intermediate would be hydrogen.

Furthermore, in the process of the present invention a different final intermediate (carboxylic functionality is not protected) is obtained compared to WO 2014/152763 (which uses a PMB protecting group) and during the different final deprotection conditions, the active pharmaceutical ingredient precipitates in the present invention during deprotection.

The present invention thus relates to a method for preparing a compound of formula

I

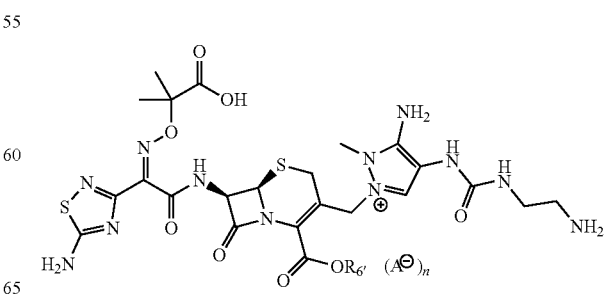

wherein
R_{6'} is hydrogen or a negative charge, and
$A^{\ominus}$ is an anion, with the condition that n is zero when $R_{6'}$ is a negative charge, and n is one when $R_{6'}$ is hydrogen,
comprising the steps of
a) preparing a compound of formula

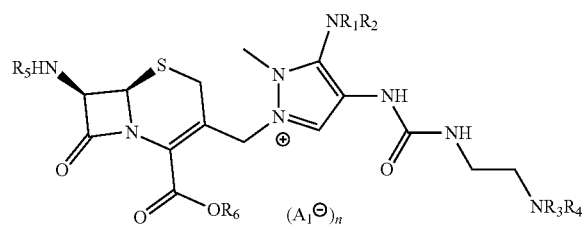

II wherein
$R_1$, $R_2$, $R_3$ and $R_4$ are independently an amino protecting group or hydrogen with the condition that $R_4$ is not hydrogen if $R_3$ is hydrogen, or $R_1$ and $R_2$, and/or $R_3$ and $R_4$ are bound together by a cyclic amino protecting group,
$R_5$ is trialkylsilyl, most preferably trimethylsilyl, or hydrogen,
$R_6$ is trialkylsilyl, most preferably trimethylsilyl, hydrogen or a negative charge, and
$A_1^{\ominus}$ is an anion, with the condition that n is zero when $R_6$ is a negative charge, and n is one when $R_6$ is trialkylsilyl, most preferably trimethylsilyl, or hydrogen,
which comprises the steps of
a-i) reacting a compound of formula

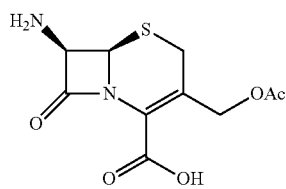

III with a silylating agent, optionally in presence of a catalyst, and
with iodotrialkylsilane, most preferably iodotrimethylsilane, a-ii) providing a compound of formula

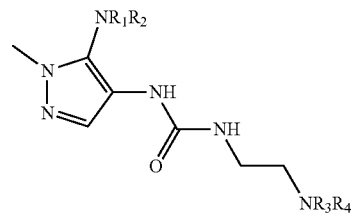

IV wherein
$R_1$-$R_4$ are as defined above, and
optionally reacting this compound of formula IV with a silylating agent,
a-iii) reacting the products of steps a-i) and a-ii),
a-iv) and optionally desilylating the product of step a-iii)
b) preparing a compound of formula

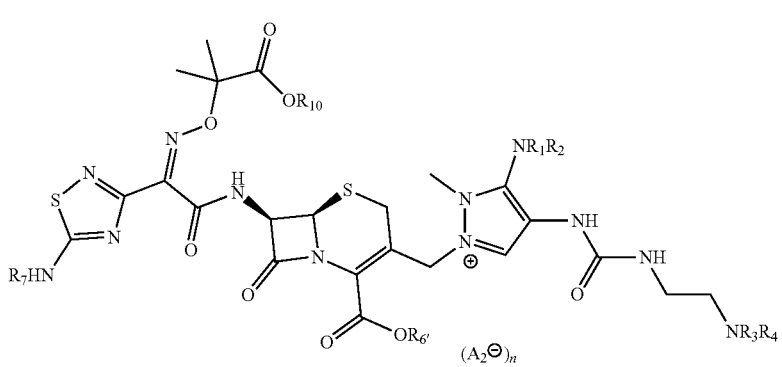

V wherein
$R_1$-$R_4$ and $R_{6'}$ are as defined above,
$R_7$ is hydrogen or an amino protecting group,
$R_{10}$ is an ester protecting group, preferably allyl, benzyl, tert-butyl, methyl, alkoxyalkyl or benzhydryl, most preferably tert-butyl, and
$A_2^{\ominus}$ is an anion, with the condition that n is zero when $R_{6'}$ is a negative charge, and
n is one when $R_{6'}$ is trialkylsilyl, more preferably trimethylsilyl, or hydrogen, most preferably hydrogen,
which comprises the step of
reacting the compound of formula II with a compound of formula

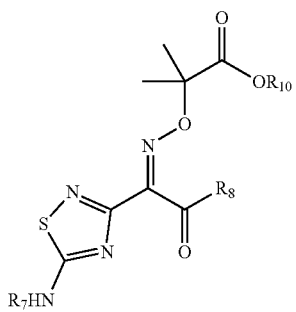

VI wherein $R_7$ and $R_{10}$ are as defined above, $R_8$ is Cl or $SR_9$, wherein $R_9$ is $C_1$-$C_6$ straight or branched alkyl, $C_3$-$C_6$ cycloalkyl, or a substituted or unsubstituted mono- or bicyclic aryl or heteroaryl ring system of 5 to 12 atoms and where each monocyclic ring contains 0 to 3 hetero atoms, and each bicyclic ring contains 0 to 4 hetero atoms selected from N, O and S, and c) removing any protecting groups from the compound of formula V to produce a compound of formula I, d) if in the compound of formula I produced in step c) $R_{6'}$ is a negative charge and n is zero optionally treating the compound of formula I produced in step c) with an acid to produce a compound of formula I, wherein $R_{6'}$ is hydrogen and n is one, e) optionally exchanging the anion by a different anion in the compound of formula I produced in step d) or in the compound of formula I produced in step c) if $R_{6'}$ is hydrogen and n is one.

As noted above, a silylation of the compound of formula IV with a silylating agent can optionally be carried out in step a-ii) of the method according to the present invention. Accordingly, the term "product of step a-ii)" as used herein either refers to the compound of formula IV itself or to the product which is obtained by reacting the compound of formula IV with a silylating agent. Preferably, the product of step a-ii) is the product of the reaction between the compound of formula IV and a silylating agent and thus, the present invention preferably relates to a method for preparing a compound of formula

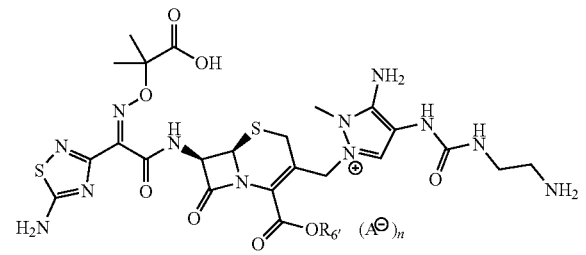

I wherein $R_{6'}$ is hydrogen or a negative charge, and $A^{\ominus}$ is an anion, with the condition that n is zero when $R_{6'}$ is a negative charge, and n is one when $R_{6'}$ is hydrogen, comprising the steps of a) preparing a compound of formula

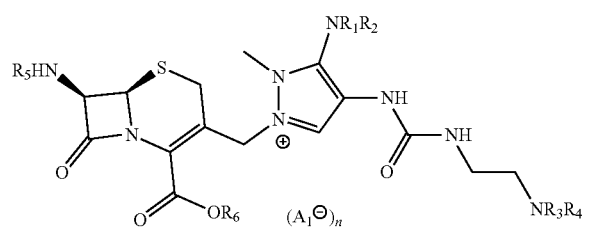

II wherein $R_1$, $R_2$, $R_3$ and $R_4$ are independently an amino protecting group or hydrogen with the condition that $R_4$ is not hydrogen if $R_3$ is hydrogen, or $R_1$ and $R_2$, and/or $R_3$ and $R_4$ are bound together by a cyclic amino protecting group, $R_5$ is trialkylsilyl, most preferably trimethylsilyl, or hydrogen, $R_6$ is trialkylsilyl, most preferably trimethylsilyl, hydrogen or a negative charge, and $A_1^{\ominus}$ is an anion, with the condition that n is zero when $R_6$ is a negative charge, and n is one when $R_6$ is trialkylsilyl, most preferably trimethylsilyl, or hydrogen, which comprises the steps of a-i) reacting a compound of formula

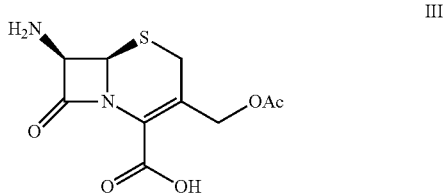 [SMILES: CC(=O)OCC1=C(C(=O)O)N2C(=O)[C@@H](N)[C@H]2SC1]

III with a silylating agent, optionally in presence of a catalyst, and with iodotrialkylsilane, most preferably iodotrimethylsilane, a-ii) reacting a compound of formula

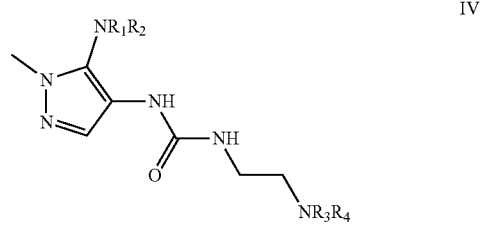

IV wherein $R_1$-$R_4$ are as defined above, with a silylating agent, a-iii) reacting the products of steps a-i) and a-ii), a-iv) and optionally desilylating the product of step a-iii)

b) preparing a compound of formula

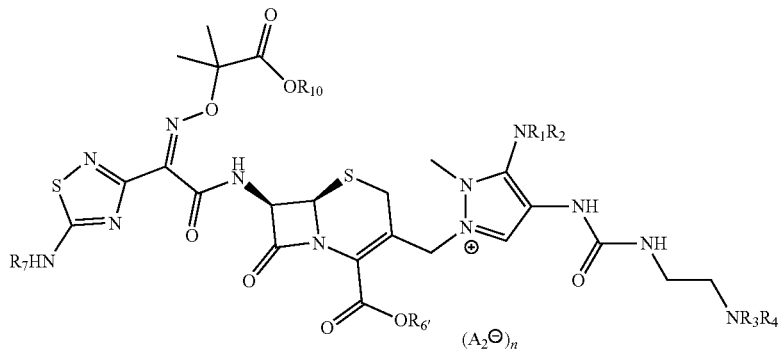

V wherein
$R_1$-$R_4$ and $R_{6'}$ are as defined above,
$R_7$ is hydrogen or an amino protecting group,
$R_{10}$ is an ester protecting group, preferably allyl, benzyl, tert-butyl, methyl, alkoxyalkyl or benzhydryl, most preferably tert-butyl, and
$A_2^{\ominus}$ is an anion, with the condition that n is zero when $R_{6'}$ is a negative charge, and
n is one when $R_{6'}$ is trialkylsilyl, more preferably trimethylsilyl, or hydrogen, most preferably hydrogen, which comprises the step of
reacting the compound of formula II with a compound of formula

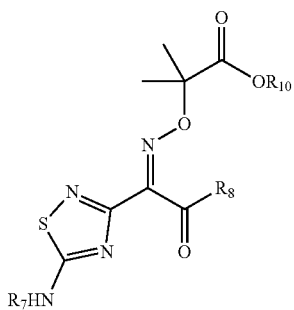

VI wherein $R_7$ and $R_{10}$ are as defined above,
$R_8$ is Cl or $SR_9$, wherein $R_9$ is $C_1$-$C_6$ straight or branched alkyl, $C_3$-$C_6$ cycloalkyl, or a substituted or unsubstituted mono- or bicyclic aryl or heteroaryl ring system of 5 to 12 atoms and where each monocyclic ring contains 0 to 3 hetero atoms, and each bicyclic ring contains 0 to 4 hetero atoms selected from N, O and S, and
c) removing any protecting groups from the compound of formula V to produce a compound of formula I,
d) if in the compound of formula I produced in step c) $R_{6'}$ is a negative charge and n is zero optionally treating the compound of formula I produced in step c) with an acid to produce a compound of formula I, wherein $R_{6'}$ is hydrogen and n is one,
e) optionally exchanging the anion by a different anion in the compound of formula I produced in step d) or in the compound of formula I produced in step c) if $R_{6'}$ is hydrogen and n is one.

The reaction conditions for carrying out coupling step a-iii) are the same irrespective of whether or not the compound of formula IV was reacted with a silylating agent in step a-ii).

It is emphasized that the silylation of the compound of formula IV in step a-ii) can optionally be carried out in each and every preferred embodiment of the method according to the present invention as described herein below, which means that in step a-ii) of each and every preferred embodiment described below, the compound of formula IV can be reacted with a silylating agent before reacting the product of steps a-i) and step a-ii) in the coupling step a-iii).

Suitable amino protecting groups in the present invention include, e.g., aryl lower alkyl such as mono-, di- or triphenyl lower alkyl (e.g., benzyl, phenethyl, benzhydryl, trityl), lower alkoxycarbonyl and an acyl group, such as lower alkanoyl.

"Lower" herein means $C_1$-$C_6$, if nothing else is obvious or indicated. So, for example, lower alkyl means herein $C_1$-$C_6$ if nothing else is indicated or obvious to the skilled person;

Aryl herein, e.g., refers to phenyl or naphthyl, phenyl being more preferred if nothing else is obvious or indicated.

Substituents herein are, e.g., selected from lower alkyl, lower alkenyl, phenyl, aryl lower alkyl, aryl lower alkenyl, hydroxy, hydroxy lower alkyl, halo, and haloalkyl.

Acyl herein refers to lower alkanoyl (e.g., formyl, acetyl, propionyl, hexanoyl, pivaloyl, etc.), mono or di or tri halo lower alkanoyl (e.g., chloroacetyl, trifluoroacetyl, etc.), lower alkoxycarbonyl (e.g., methoxycarbonyl, ethoxycarbonyl, tert-butoxycarbonyl, tert-pentyloxycarbonyl, hexyloxycarbonyl, etc.), carbamoyl, aroyl (e.g., benzoyl, toluoyl, naphthoyl, etc.), aryl lower alkanoyl (e.g., phenylacetyl, phenylpropionyl, etc.), aryloxycarbonyl (e.g., phenoxycarbonyl, naphthyloxycarbonyl, etc.), aryloxy lower alkanoyl (e.g., phenoxyacetyl, phenoxypropionyl, etc.), arylglyoxyloyl (e.g., phenylglyoxyloyl, naphthylglyoxyloyl, etc.), and aryl lower alkoxycarbonyl which is optionally substituted by suitable substituent(s) such as nitro, halogen or lower alkyl substituents (e.g., benzyloxycarbonyl, phenethyloxycarbonyl, p-nitrobenzyloxycarbonyl, etc).

The term "cyclic amino protecting group" includes all amino protecting groups that, when bound to the nitrogen atom of the amino group, form a cyclic system incorporating that nitrogen atom. The term therefore includes groups that form cyclic imido groups, such as succinimide and, particularly, phthalimide groups.

Preferable examples of "amino protecting groups" herein include triphenylmethyl (trityl, Tr), benzyl (can be cleaved off the protected amino group by use of hydrogen), allyl, carbamate forming protecting groups such as benzyloxycarbonyl (Cbz), allyloxycarbonyl (Aloc), 9-fluorenylmethoxycarbonyl (Fmoc), tert-butoxycarbonyl (Boc), 2-(trimethylsilyl)ethoxycarbonyl (Teoc), 2,2,2-trichloroethoxycarbonyl (Troc), a silyl group (e.g. TMS), STABASE (—Si(CH$_3$)$_2$—CH$_2$CH$_2$—(CH$_3$)$_2$Si—), Benzostabase, and triazinanone forming protecting groups (so that protection of the amino group is as triazinanone).

In one embodiment of the present invention at least one of $R_1$ and $R_2$ is an amino protecting group, preferably triphenylmethyl (Tr), trialkylsilyl, preferably trimethylsilyl (TMS), tert-butyldimethylsilyl (TBS) or triisopropylsilyl (TIPS), or tert-butyldiphenylsilyl (TBDPS), STABASE (—Si(CH$_3$)$_2$—CH$_2$H$_2$CH—(CH$_3$)$_2$Si—), Benzostabase, N-(triphenylphosphoranylidene) or $R_1$ and $R_2$ are both benzyl or both allyl. In a preferred embodiment of the present invention at least one of $R_1$ and $R_2$ is triphenylmethyl (Tr), trialkylsilyl, preferably trimethylsilyl (TMS), tert-butyldimethylsilyl (TBS) or triisopropylsilyl (TIPS), or tert-butyldiphenylsilyl (TBDPS) or $R_1$ and $R_2$ are both benzyl or both allyl. It is most preferred that one of $R_1$ and $R_2$ is triphenylmethyl. In one embodiment, at least one of $R_1$ and $R_2$ is not hydrogen.

In one embodiment of the present invention at least one of $R_3$ and $R_4$ is an amino protecting group, preferably tert-butyloxycarbonyl (Boc), triphenylmethyl, benzyloxycarbonyl (Cbz), allyloxycarbonyl (Aloc), 9-fluorenylmethoxycarbonyl (Fmoc), methoxycarbonyl, ethoxycarbonyl, 2-(tri methylsilyl)ethoxycarbonyl (Teoc), 2,2,2-trichloroethoxycarbonyl (Troc), or part of a triazinanone (so that protection of the amino group is as triazinanone) or trimethylsilyl or $R_3$ and $R_4$ are both benzyl, allyl, or (p-methoxybenzyl). In a preferred embodiment, $R_3$ and/or $R_4$ is/are (a) carbamate forming protecting group(s). More preferably, at least one of $R_3$ and $R_4$ is tert-butyloxycarbonyl. In the present invention, at least one of $R_3$ and $R_4$ is not hydrogen.

$R_5$ and $R_6$ in the present invention are trialkylsilyl.

In the present invention trialkylsilyl refers to a group of the formula —Si(R')(R'')(R''') wherein each of R', R'', and R''' are independently $C_1$-$C_6$ alkyl. An example of trialkylsilyl in the present invention is in particular trimethylsilyl. Other examples are, e.g., t-butyldimethylsilyl (TBS) or triisopropylsilyl (TIPS).

In one preferred embodiment of the present invention $R_5$ and $R_6$ are trimethylsilyl.

In one embodiment of the present invention $R_7$ is hydrogen. Compared to the originator synthesis of ceftolozane a (Boc) protection of the respective amino group can be avoided, making the approach of the present invention shorter and more cost effective with a higher atom economy and less waste stream.

$R_8$ in the present invention is Cl or $SR_9$. If $R_9$ is a substituted mono- or bicyclic aryl or heteroaryl ring system of 5 to 12 atoms and where each monocyclic ring contains 0 to 3 hetero atoms, and each bicyclic ring contains 0 to 4 hetero atoms selected from N, O and S, the mono- or bicyclic aryl or heteroaryl ring system carries, e.g., 1-3 substituents selected from lower alkyl, lower alkenyl, phenyl, aryl lower alkyl, aryl lower alkenyl, hydroxy, hydroxy lower alkyl, halo, and haloalkyl.

In one embodiment of the present invention $R_8$ is Cl or

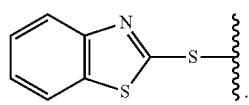 [SMILES: *Sc1nc2ccccc2s1]

$R_{10}$ in the present invention is an ester protecting group. Suitable ester protecting groups used in the present invention are, e.g., methyl, tert-butyl, allyl, benzyl, alkoxyalkyl (e.g. $C_1$-$C_4$ alkyoxy $C_1$-$C_4$ alkyl), diphenylmethyl (benzhydryl). Preferably $R_{10}$ is tert-butyl, methyl, alkoxyalkyl or benzhydryl in the present invention. More preferably, $R_{10}$ is tert-butyl in the present invention.

In a preferred embodiment, one of $R_1$ and $R_2$ is triphenylmethyl, at least one of $R_3$ and $R_4$ is a carbamate forming protecting group and $R_7$ is hydrogen.

The anion (shown as $A^\ominus$, $A_1^\ominus$, $A_2^\ominus$ in the compounds of formulae I, II, V and shown as $A_3^\ominus$ in the compound of formula VII, see below) does not necessarily have to be a monovalent anion in the present invention. It can, e.g., also be a di- or trivalent anion. The anion could then be associated with 2 or 3 compounds as shown carrying one positive charge, each.

The anions $A^\ominus$, $A_1^\ominus$, $A_2^\ominus$ and $A_3^\ominus$ are not necessarily the same and can be different throughout the process. For example, in one embodiment, $A^\ominus$ is hydrogen sulfate, $A_1^\ominus$ is iodide, $A_2^\ominus$ is trifluoroacetate and $A_3^\ominus$ is formate.

The anion $A^\ominus$ in the compound of formula I is preferably $HSO_4^-$.

In a preferred embodiment of the present invention, $R_{6'}$ is hydrogen and n is one. In one embodiment, $R_{6'}$ is hydrogen, n is one and $A^\ominus$ is $HSO_4^-$ in the compound of formula I. When $R_6$ is trimethylsilyl or hydrogen in the compound of formula II and n is one, the anion $A_1^\ominus$ in the compound of formula II is, e.g., iodide.

The silylating agent in the present invention is one that substitutes a hydrogen atom bound to an oxygen or nitrogen atom by a trialkylsilyl group, preferably by a trimethylsilyl (Si(CH3)3) group. Preferably, the silylating agent herein is e.g. selected from the group of hexamethyldisilazane (HMDS), N,O-bis-(trimethylsilyl)-acetamide (BSA), N,O-bis-(trimethylsilyl)trifluoroacetamide (BSTFA), chlorotrimethylsilane (TMCS), bromotrimethylsilane (TMBS), iodotrimethylsilane (TMJS), trimethylsilyl trifluoromethanesulfonate (TMSOTf), N-Methy-N-trimethylsilylacetamide (MSA) and methyltrimethylsilyltrifluoroacetamide (MSTFA). HMDS is more preferably used as silylating agent in step a-i) of the present invention. TMJS is also a preferred catalyst in step a-i). BSA is more preferably used as silylating agent in step a-ii) of the present invention.

In step a) of the present invention a compound of formula II is prepared.

In step a-i) a compound of formula III is preferably first treated with the silylating agent, optionally in presence of a catalyst (which can be catalytic amounts of TMJS), and then treated with iodotrialkylsilane to produce the alkyl iodide. In the present invention, iodotrialkylsilane refers to a group of the formula (R')(R'')(R''')SiI where each of R', R'', and R''' are independently $C_1$-$C_6$ alkyl. The preferred iododtrialkylsilane used in the present is iodotrimethylsilane (TMJS). For production of the alkyl iodide in step a-i) in the present invention, it is thus preferable to use TMJS (in substantial amounts).

The reaction product of step a-i) (with preferred trimethylsilyl groups) is shown below

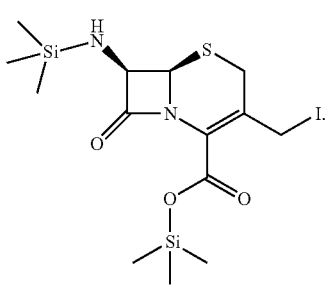 [SMILES: C[Si](C)(C)N[C@@H]1C(=O)N2C(C(=O)O[Si](C)(C)C)=C(CI)CS[C@H]12]

Preferably steps a-i) and a-ii) (if the silylation reaction takes place) are independently conducted in one or a combination of two or more solvents selected from the group consisting of N-methyl-2-pyrrolidone, 1,3-dimethyl-3,4,5,6-tetrahydro-2(1H)-pyrimidinone, dimethylacetamide, 1,3-dimethyl-2-imidazolidinone, dimethylformamide, dimethyl sulfoxide or methylene chloride. CH2Cl2 is, e.g., used as solvent in step a-i). NMP is, e.g., used as solvent in step a-ii) (if the silylation takes place)

Preferably, a base is present in step a-ii) (if the silylation reaction takes place) and preferably the base is 1,8-bis(N,N-dimethylamino)-naphthalin, a tertiary amine (such as triethyl amine), a salt of trifluoro acetic acid (such an alkali or earth alkali salts) or a sterically hindered pyridine (such as 2,6-di-tert-butyl-pyridine). More preferably, 1,8-bis(N,N-dimethylamino)-naphthalin is used as base in step a-ii) of the present invention. 1,8-Bis(N,N-dimethylamino)-naphthalin is commercially available under the tradename proton Sponge®.

In one embodiment, the silylated 7-ACA intermediate is dried before redissolving in a solvent and activation with iodotrialkylsilane (preferably with TMJS). The activation reaction of the (silylated) 7-ACA with TMJS is preferably conducted at ≤0° C. (e.g. −5° C.) for 6-16 hours.

The reaction product of step a-i) of the present invention is combined with the product of step a-ii) of the present invention in step a-iii), preferably by dropwise addition of the former to the latter. The reaction of the products of steps a-i) and a-ii) can be conducted at room temperature (20-25° C.).

The coupling step a-iii) can optionally be carried out in the presence of a metal catalyst. In this embodiment, wherein the coupling step a-iii) is carried out in the presence of a metal catalyst, the method of the present invention thus relates to a method for preparing a compound of formula

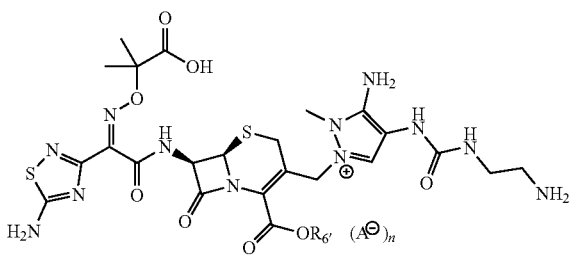

I wherein $R_{6'}$ is hydrogen or a negative charge, and $A^{\ominus}$ is an anion, with the condition that n is zero when $R_{6'}$ is a negative charge, and n is one when $R_{6'}$ is hydrogen, comprising the steps of a) preparing a compound of formula

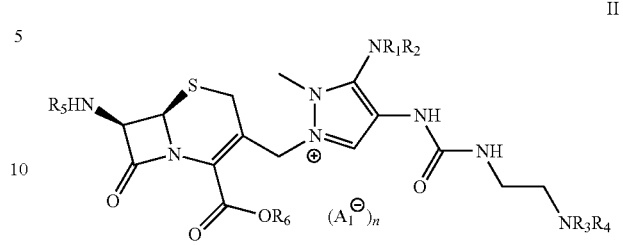

II wherein $R_1$, $R_2$, $R_3$ and $R_4$ are independently an amino protecting group or hydrogen with the condition that $R_4$ is not hydrogen if $R_3$ is hydrogen, or $R_1$ and $R_2$, and/or $R_3$ and $R_4$ are bound together by a cyclic amino protecting group, $R_5$ is trialkylsilyl, most preferably trimethylsilyl, or hydrogen, $R_6$ is trialkylsilyl, most preferably trimethylsilyl, hydrogen or a negative charge, and $A_1^{\ominus}$ is an anion, with the condition that n is zero when $R_6$ is a negative charge, and n is one when $R_6$ is trialkylsilyl, most preferably trimethylsilyl, or hydrogen, which comprises the steps of a-i) reacting a compound of formula

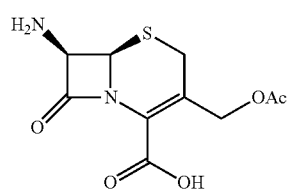

III with a silylating agent, optionally in presence of a catalyst, and with iodotrialkylsilane, most preferably iodotrimethylsilane, a-ii) providing a compound of formula

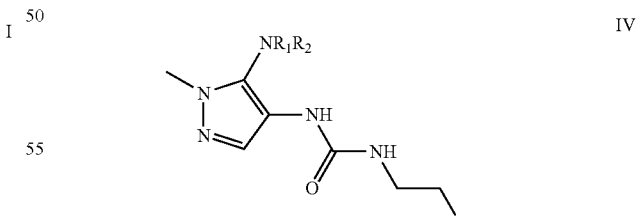

IV wherein $R_1$-$R_4$ are as defined above, and optionally reacting this compound with a silylating agent, a-iii) reacting the products of steps a-i) and a-ii) in the presence of a metal catalyst, a-iv) and optionally desilylating the product of step a-iii)

b) preparing a compound of formula

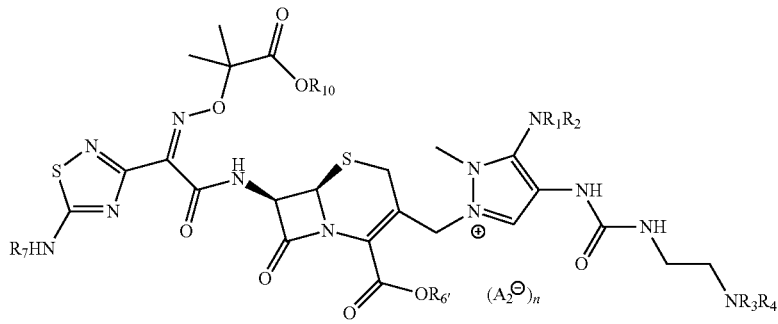

V wherein
$R_1$-$R_4$ and $R_6$ are as defined above,
$R_7$ is hydrogen or an amino protecting group,
$R_{10}$ is an ester protecting group, preferably allyl, benzyl, tert-butyl, methyl, alkoxyalkyl or benzhydryl, most preferably tert-butyl, and
$A_2^{\ominus}$ is an anion, with the condition that n is zero when $R_{6'}$ is a negative charge, and
n is one when $R_{6'}$ is trialkylsilyl, more preferably trimethylsilyl, or hydrogen, most preferably hydrogen,
which comprises the step of
reacting the compound of formula II with a compound of formula

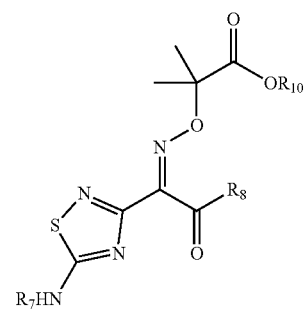

VI wherein $R_7$ and $R_{10}$ are as defined above,
$R_8$ is Cl or $SR_9$, wherein $R_9$ is $C_1$-$C_6$ straight or branched alkyl, $C_3$-$C_6$ cycloalkyl, or a substituted or unsubstituted mono- or bicyclic aryl or heteroaryl ring system of 5 to 12 atoms and where each monocyclic ring contains 0 to 3 hetero atoms, and each bicyclic ring contains 0 to 4 hetero atoms selected from N, O and S, and
c) removing any protecting groups from the compound of formula V to produce a compound of formula I,
d) if in the compound of formula I produced in step c) $R_{6'}$ is a negative charge and n is zero optionally treating the compound of formula I produced in step c) with an acid to produce a compound of formula I, wherein $R_{6'}$ is hydrogen and n is one,
e) optionally exchanging the anion by a different anion in the compound of formula I produced in step d) or in the compound of formula I produced in step c) if $R_{6'}$ is hydrogen and n is one.

In order to avoid repetition in the present description of the method according to the invention, it is emphasized that the metal catalyst can optionally be used in step a-iii) of each and every (preferred) embodiment of the present invention as described herein.

The use of a metal catalyst in coupling step a-iii) allows a metal-mediated reaction which compared to the non-metal catalyzed reactions results in higher yields and/or cleaner formation of the desired coupling product.

Typical metals for said metal catalyst can be selected from iron (Fe), ruthenium (Ru), cobalt (Co), rhodium (Rh), nickel (Ni), iridium (Ir), palladium (Pd), and platinum (Pt).

Preferably, the metal of said metal catalyst useful in coupling steps a-iii) is palladium (Pd). Reference is made to the disclosure of WO 2016/025839 A1, the disclosure of which is incorporated herein by reference. Thus, the metal catalyst optionally used in step a-iii) of the method of the present invention is preferably a palladium catalyst as described in more detail herein below. In order to avoid repetition in the present description of the method according to the invention, it is emphasized that the palladium catalyst can optionally be used in each and every (preferred) embodiment of the present invention as described herein.

In particular on pages 11, paragraph [0070] to page 19, paragraph [0094] and on page 28, paragraph [0161] to page 31, paragraph [0166], WO 2016/025839 A1 describes palladium catalysts comprising a palladium(0)- or palladium (II)-source and one or more palladium-binding ligands. These palladium catalysts described as in WO 2016/025839 A1 are suitable for use as metal catalysts in the method of the present invention, and are therefore incorporated herein by reference. The following palladium sources from WO 2016/025839 A1 are in particular useful in the method of the present invention. tris(dibenzylideneacetone)dipalladium (0), or solvates thereof, allylpalladium(II) chloride dimer, tetrakis(triphenylphosphine)palladium, palladium(II) acetate, palladium(II) trifluoroacetate, palladium(II) chloride, palladium(II) bromide, and bis(acetonitrile)dichloropalladium(II). any type of pre-catalysts capable of expulging a Pd(0)-species, such as the Buchwald-type palladacycles (2-aminobiphenylpalladium or 2-aminoethylphenylpalladium palladacycles)

Ligands that can be used as palladium binding ligands include phosphites or phosphines. The ligand serves to stabilize the intermediate species within the palladium catalysis cycle while facilitating the formation of the desired coupling product.

Suitable phosphine ligands from WO 2016/025839 A1 for use in the present invention include triphenylphosphine, tri-tert-butylphosphine, 2-dicyclohexylphosphino-2',6'-diisopropoxybiphenyl (RuPhos), 2-dicylcohexylphosphino-2', 4',6'-triisopropylbiphenyl (XPhos), 4,5-bis(diphenylphosphino)-9,9'-dimethylxanthine (Xantphos), 1,2-bis(diphenylphosphino)ethane (dppe), and 1,3-bis(diphenylphosphino)propane (dppp).

Particularly suitable phosphite ligands from WO 2016/025839 A1 for use in the present invention include electron-rich aromatic phosphite ligands of the type P(OAr)$_3$, wherein each Ar can be individually defined as follows:

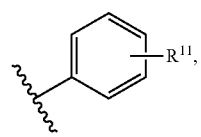

wherein $R^{11}$ is an electron donating group, such as $C_1$-$C_6$-alkyl, O—$C_1$-$C_6$-alkyl, N—$C_1$-$C_6$-dialkyl, N-piperidinyl, N-pyrrolidinyl, N—N'—$C_1$-$C_6$-alkyl piperazinyl. Furthermore, the aryl residues can be additionally linked to each other.

In a preferred embodiment, the phosphite ligand is

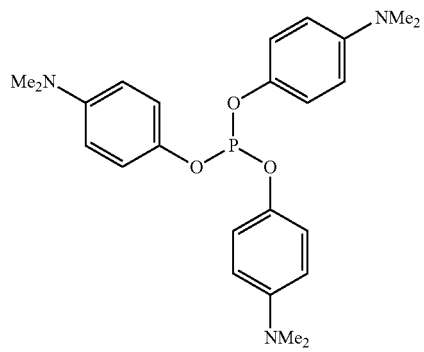 [SMILES: CN(C)c1ccc(OP(Oc2ccc(N(C)C)cc2)Oc2ccc(N(C)C)cc2)cc1]

Typically, a substoichiometric amount of both the palladium source and of the palladium-binding ligand(s) is used in the coupling reaction. For example, the palladium source can be present in an amount of from about 0.2 mol-% to about 5 mol-% with respect to the compound of formula III.

The molar ratio of palladium binding ligand to palladium is typically in a range of from about 1:1 to about 10:1, preferably in a range of from about 3:1 to about 6:1.

The palladium catalyst can be formed in-situ, i.e. in the course of the coupling reaction carried out in step a-iii) by means of including into the reaction mixture a suitable palladium source and a suitable palladium-binding ligand as separate reagents. In such cases, the palladium source and the palladium-binding ligand forms the active palladium catalyst within the reaction mixture. In a preferred embodiment, the palladium source comprises tris(dibenzylideneacetone)dipalladium(0) and the palladium-binding ligand is:

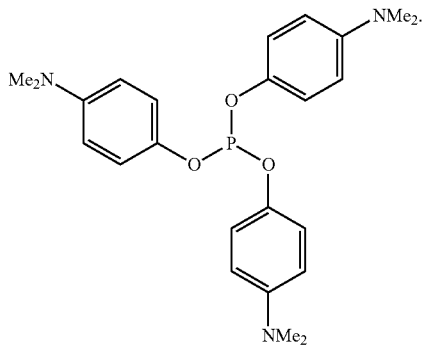 [SMILES: CN(C)c1ccc(OP(Oc2ccc(N(C)C)cc2)Oc2ccc(N(C)C)cc2)cc1]

Alternatively, the palladium catalyst can be used as a pre-complexed palladium catalyst already including the palladium source and the palladium-binding ligand. Such a pre-complexed palladium catalyst is e.g. tetrakis(triphenylphosphine)palladium(0) which includes both a palladium(0) source and the palladium-binding ligand triphenylphosphine. The reaction conditions for carrying out the coupling step a-iii) in the presence of a palladium catalyst can be adopted from WO 2016/025839 A1. Reference is particularly made to "Methods of Making" as described under item 6.3 of WO 2016/025839 A1 (page 25, paragraph [0151] to page 39, paragraph [0193]). The conditions for carrying out the coupling in the presence of a palladium catalyst are incorporated herein by reference, and can be used analogously for the coupling of the products of steps a-i) and a-ii) in coupling step a-iii) Preferably, the reaction product of step a-iii) is not desilylated. Thereby the overall process can be shortened. In one embodiment, $R_5$ and $R_6$ in the compound of formula II that is produced in step a) and that is then used in step b) are thus trialkylsilyl, more preferably trimethylsilyl.

In step b) of the present invention a compound of formula V is prepared. Therefore, the compound of formula II is reacted with the compound of formula VI. Preferably, the compound of formula II is not isolated from the reaction mixture of step a) before it is reacted with the compound of formula VI in step b). The alkylation and amide coupling can thus be done in a one-pot procedure without intermediate isolation of the cephem core carrying the pyrazole moiety.

The compound of formula VI wherein $R_8$ is Cl is, e.g., prepared by treating the compound of formula

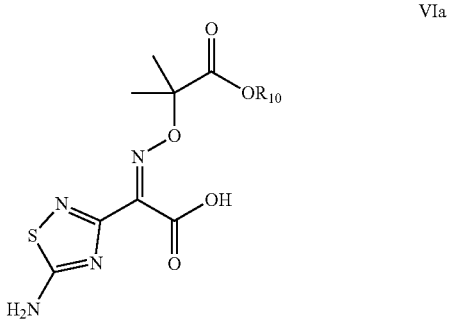

with oxalyl chloride or PCs. Dimethylformamide (DMF) can be used as catalyst in the reaction. A suitable solvent for the reaction is, e.g., methylene chloride.

The compound of formula VI wherein $R_8$ is

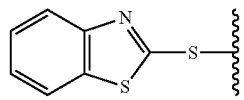 [SMILES: *Sc1nc2ccccc2s1]

is, e.g., prepared by treating the compound of formula VIa with triphenylphosphine (PPh$_3$) and 2,2'-dithiobis(benzothiazole) and a base (e.g. triethylamine). A suitable solvent for the reaction is, e.g., methylene chloride.

Step b) of the present invention can, e.g., be conducted in N-methyl-2-pyrrolidone, 1,3-dimethyl-3,4,5,6-tetrahydro-2 (1H)-pyrimidinone, dimethylacetamide, 1,3-dimethyl-2-imidazolidinone, dimethylformamide, dimethyl sulfoxide, methylene chloride or mixtures thereof as solvents. The reaction temperature preferably remains at ≤5° C. The reaction of step b) is preferably quenched with an aqueous quenching solution (e.g. a NaHCO$_3$ solution) and the aqueous phase is then extracted by an organic solvent (e.g. methylene chloride). An aqueous workup is then suitably conducted with the organic phase, where preferably a mildly acidic (pH 4-6) aqueous solution is used. In one embodiment the worked up organic phase is then mixed with sodium trifluoroacetate. Thereby, the compound of formula V, wherein Re is hydrogen, n is one and $A_2^\ominus$ is trifluoroacetate, is obtainable as a precipitate. In one embodiment of the method of the present invention a compound of formula V is thus prepared in step b) wherein $R_{6'}$ is hydrogen, n is one and $A_2^\ominus$ is trifluoroacetate.

In step c) of the present invention any protecting groups from the compound of formula V are removed to produce a compound of formula I. If in the compound of formula I produced in step c) $R_{6'}$ is a negative charge and n is zero an optional step d) can be conducted wherein the compound of formula I produced in step c) is treated with an acid to produce a compound of formula I, wherein $R_{6'}$ is hydrogen and n is one. In an optional step e) the anion in the compound of formula I produced in step d) or in the compound of formula I produced in step c), if $R_{6'}$ is hydrogen and n is one, can further be exchanged by a different anion. In the present invention, removal of the protecting groups (deprotection) can be achieved, unless otherwise indicated, under conditions known in the art and by the skilled person, and depending on the protection group that has been used. Representative methods and suitable protecting groups, including for amino protecting groups are described, for example, in T. W. Greene and G. M. Wuts, *Protecting Groups in Organic Synthesis*, 3$^{rd}$ Ed., Wiley N. Y., 1999, and references cited therein.

In a preferred method of the present invention one or more acids are used in step c) for removing any protecting groups from the compound of formula V to produce a compound of formula I, wherein $R_{6'}$ is hydrogen and n is one. Protective group removal by use of one or more acids in step c) can be stepwise (wherein, e.g., first triphenylmethyl groups are removed from the compound of formula V, wherein at least $R_1$ is triphenylmethyl and $R_2$ is hydrogen, before all other protective groups are removed) or any protective groups from the compound of formula V can be removed in one step to produce the compound of formula I.

Preferably, $A^\ominus$ in the compound of formula I is an anion deriving from an acid preferably used in step c) of the present invention and $R_{6'}$ is hydrogen and n is one. More preferably, $A^\ominus$ in the compound of formula I is $HSO_4^-$, $R_{6'}$ is hydrogen and n is one. If in step c) a compound of formula I is produced wherein the anion is not $HSO_4^-$, the anion in the compound of formula I can be exchanged in a further reaction step to produce ceftolozane sulfate.

In a preferred method of the present invention, $R_1$ and $R_2$ are independently an amino protecting group or hydrogen, with the condition that $R_1$ is not hydrogen if $R_2$ is hydrogen and $R_1$ and/or $R_2$ can be selectively removed under conditions not removing $R_3$, $R_4$, $R_7$ and $R_{10}$;

and step c) comprises a step c1) wherein $R_1$ and $R_2$ are selectively removed from the compound of formula V to produce a compound of formula

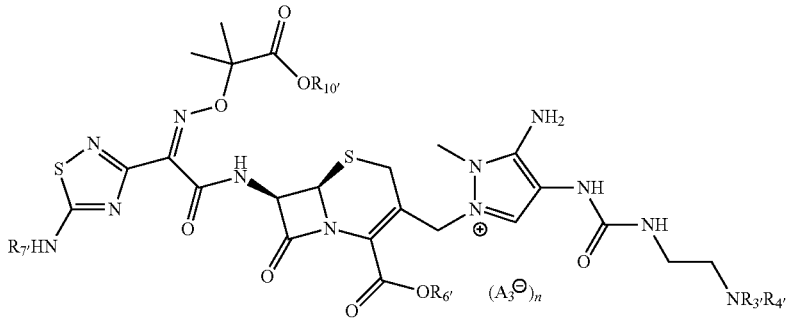

VII wherein $R_{3'}$, $R_{4'}$, $R_{6'}$, $R_{7'}$ and $R_{10'}$ are defined as $R_3$, $R_4$, $R_6$, $R_7$ and $R_{10}$ before, respectively, wherein in case one or more of $R_{3'}$, $R_{4'}$, $R_{7'}$ and $R_{10'}$ is a protecting group, said protecting group is not removed under the conditions used for removal of $R_1$ and $R_2$, and $A_3^\ominus$ is an anion, with the condition that n is zero when $R_{6'}$ is a negative charge, and n is one when $R_{6'}$ is hydrogen. Step c1) is optional n the method of the present invention for preparing a compound of formula I. No protective groups other than $R_1$ and/or $R_2$ are removed in step c1). Any remaining protective groups of the compound of formula VII are removed in a step c2). The present inventors found that selective removal of $R_1$ and/or $R_2$ is advantageous regarding the purification of the product (see below).

In a preferred method of the present invention $R_1$ is triphenylmethyl and $R_2$ is hydrogen or vice versa and step c) comprises a step c1) wherein triphenylmethyl groups are selectively removed from the compound of formula V to produce a compound of formula

VII

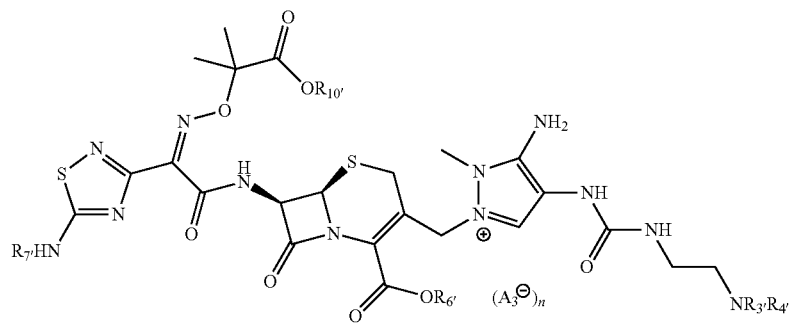

wherein
$R_{3'}$, $R_{4'}$, $R_{6'}$, $R_{7'}$ and $R_{10'}$ are defined as $R_3$, $R_4$, $R_{6'}$, $R_7$ and $R_{10}$ before, respectively with the exception that $R_{3'}$, $R_{4'}$, $R_{7'}$ and $R_{10'}$ are not triphenyl methyl and if $R_3$ and/or $R_4$ and/or $R_7$ and/or $R_{10}$ are triphenylmethyl in the compound of formula V $R_{3'}$ and/or $R_{4'}$ and/or $R_{7'}$ and/or $R_{10'}$ are hydrogen in the compound of formula VII, respectively, and
$A_3^\ominus$ is an anion, with the condition that n is zero when $R_{6'}$ is a negative charge, and n is one when $R_{6'}$ is hydrogen. Step c1) is optional in the method of the present invention for preparing a compound of formula I. No protective groups other than triphenylmethyl are removed in step c1). Any remaining protective groups of the compound of formula VII are removed in a step c2). The present inventors found that selective removal of the triphenylmethyl protecting group(s) is advantageous regarding the purification of the product (see below).

The present invention refers in another preferred embodiment to a method for preparing a compound of formula

I

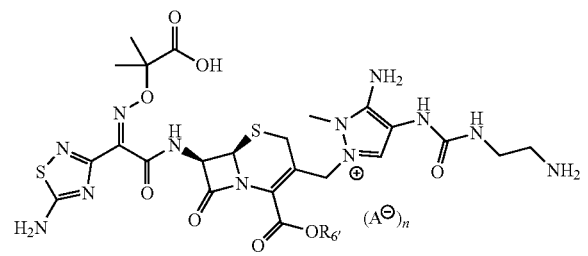

wherein
$R_{6'}$ is hydrogen or a negative charge, and
$A^\ominus$ is an anion, with the condition that n is zero when $R_{6'}$ is a negative charge, and n is one when $R_{6'}$ is hydrogen, comprising the steps of
a) preparing a compound of formula

II

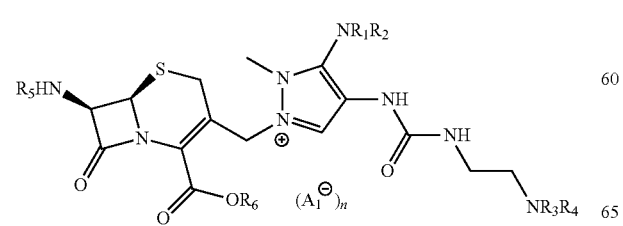

wherein
$R_1$ and $R_2$ are independently an amino protecting group or hydrogen, with the condition that $R_1$ is not hydrogen if $R_2$ is hydrogen, and $R_1$ and/or $R_2$ can be selectively removed under conditions not removing $R_3$, $R_4$, $R_7$ and $R_{10}$, wherein preferably $R_1$ is triphenylmethyl and $R_2$ is hydrogen,
$R_3$ and $R_4$ are independently an amino protecting group or hydrogen, with the condition that $R_4$ is not hydrogen if $R_3$ is hydrogen, or $R_3$ and $R_4$ are bound together by a cyclic amino protecting group, and $R_3$ and $R_4$ are selected so that they are not removed under the conditions used for removal of $R_1$ and/or $R_2$;
$R_5$ is trialkylsilyl, most preferably trimethylsilyl, or hydrogen,
$R_6$ is trialkylsilyl, most preferably trimethylsilyl, hydrogen or a negative charge, and
$A_1^\ominus$ is an anion, with the condition that n is zero when $R_6$ is a negative charge, and n is one when $R_6$ is trialkylsilyl, most preferably trimethylsilyl, or hydrogen,
which comprises the steps of
a-i) reacting a compound of formula

III

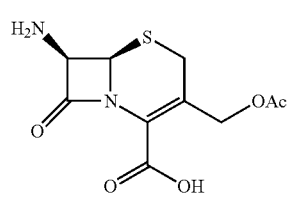

with a silylating agent, optionally in presence of a catalyst, and with iodotrialkylsilane, most preferably iodotrimethylsilane,
a-ii) providing a compound of formula

IV

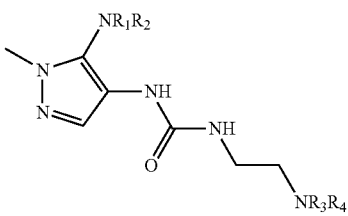

wherein
$R_1$-$R_4$ are as defined above, and
optionally reacting the compound of formula IV with a silylating agent,
a-iii) reacting the products of steps a-i) and a-ii),
a-iv) and optionally desilylating the product of step a-iii)

b) preparing a compound of formula

V

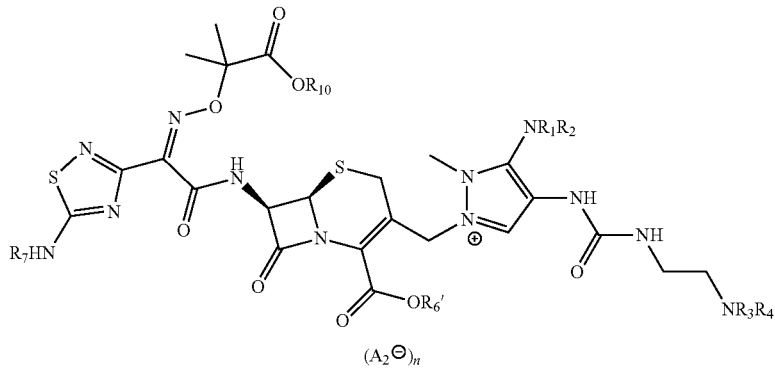

wherein
$R_1$-$R_4$ and $R_{6'}$ are as defined above,
$R_7$ is hydrogen or an amino protecting group which is not removed under the conditions used for removal of $R_1$ and/or $R_2$,
$R_{10}$ is an ester protecting group which is not removed under the conditions used for removal of $R_1$ and/or $R_2$, preferably allyl, benzyl, tert-butyl, methyl, alkoxyalkyl or benzhydryl, most preferably tert-butyl, and
$A_2^\ominus$ is an anion, with the condition that n is zero when $R_{6'}$ is a negative charge, and n is one when $R_{6'}$ is hydrogen, which comprises the step of
reacting the compound of formula II with a compound of formula

VI

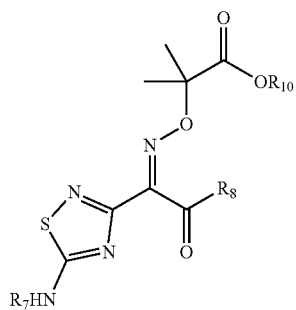

wherein $R_7$ and $R_{10}$ are as defined above, $R_8$ is Cl or $SR_9$, wherein $R_9$ is $C_1$-$C_6$ straight or branched alkyl, $C_3$-$C_6$ cycloalkyl, or a substituted or unsubstituted mono- or bicyclic aryl or heteroaryl ring system of 5 to 12 atoms and where each monocyclic ring contains 0 to 3 hetero atoms, and each bicyclic ring contains 0 to 4 hetero atoms selected from N, O and S, and c) removing any protecting groups from the compound of formula V to produce a compound of formula I, d) if in the compound of formula I produced in step c) $R_{6'}$ is a negative charge and n is zero optionally treating the compound of formula I produced in step c) with an acid to produce a compound of formula I, wherein $R_{6'}$ is hydrogen and n is one, e) optionally exchanging the anion by a different anion in the compound of formula I produced in step d) or in the compound of formula I produced in step c) if $R_{6'}$ is hydrogen and n is one, wherein step c) comprises
c1) selectively removing $R_1$ and/or $R_2$ from the compound of formula V to produce a compound of formula

VII

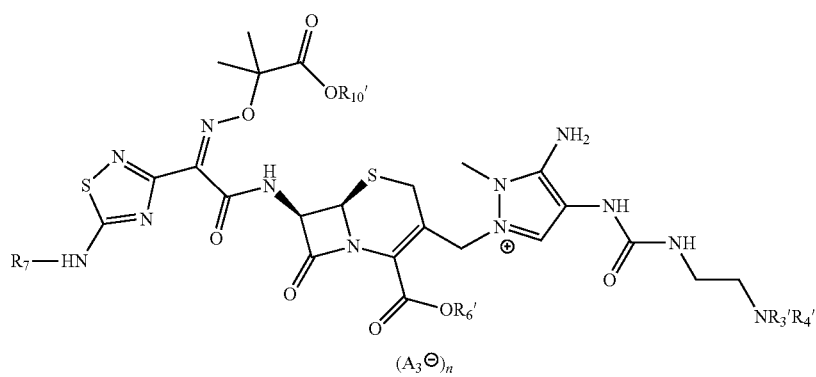

and c2) removing any remaining protecting groups of the compound of formula VII wherein $R_{3'}$, $R_{4'}$, $R_{6'}$, $R_{7'}$ and $R_{10'}$ are defined as $R_3$, $R_4$, $R_{6'}$, $R_7$ and $R_{10}$ before, respectively, and $A_3^\ominus$ is an anion, with the condition that n is zero when $R_{66'}$ is a negative charge, and n is one when $R_{6'}$ is hydrogen.

The present invention refers in a more preferred embodiment to a method for preparing a compound of formula

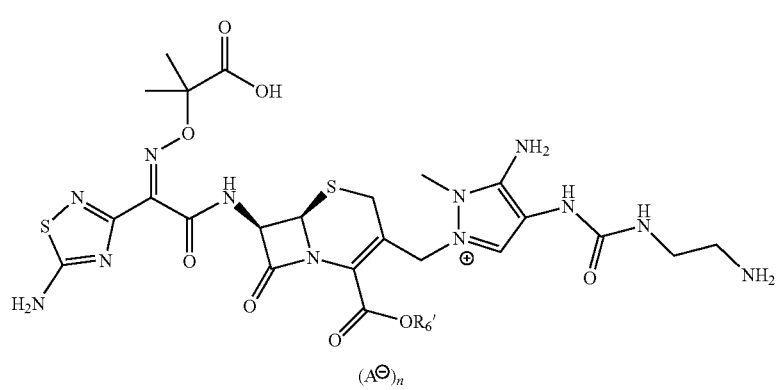

I wherein $R_{6'}$ is hydrogen or a negative charge, and $A^\ominus$ is an anion, with the condition that n is zero when $R_{6'}$ is a negative charge, and n is one when $R_{6'}$ is hydrogen, comprising the steps of a) preparing a compound of formula

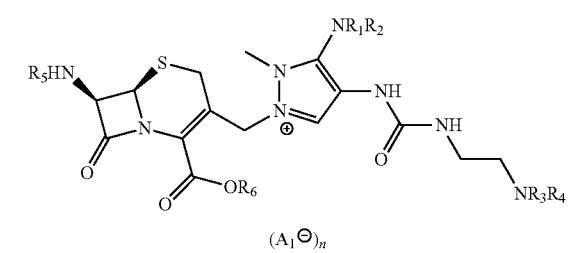

II wherein $R_1$ is triphenylmethyl and $R_2$ is hydrogen or vice versa, $R_3$ and $R_4$ are independently an amino protecting group or hydrogen with the condition that $R_4$ is not hydrogen if $R_3$ is hydrogen, or $R_3$ and $R_4$ are bound together by a cyclic amino protecting group, $R_5$ is trialkylsilyl, most preferably trimethylsilyl, or hydrogen, $R_6$ is trialkylsilyl, most preferably trimethylsilyl, hydrogen or a negative charge, and $A_1^\ominus$ is an anion, with the condition that n is zero when $R_6$ is a negative charge, and n is one when $R_6$ is trialkylsilyl, most preferably trimethylsilyl, or hydrogen, which comprises the steps of a-i) reacting a compound of formula

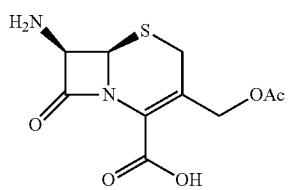

III with a silylating agent, optionally in presence of a catalyst, and with iodotrialkylsilane, most preferably iodotrimethylsilane, a-ii) providing a compound of formula

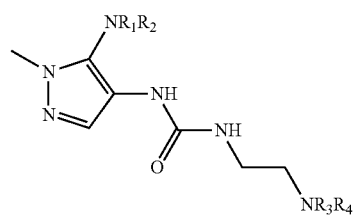

IV wherein $R_1$-$R_4$ are as defined above, and optionally reacting the compound of formula IV with a silylating agent, a-iii) reacting the products of steps a-i) and a-ii), a-iv) and optionally desilylating the product of step a-iii)

b) preparing a compound of formula

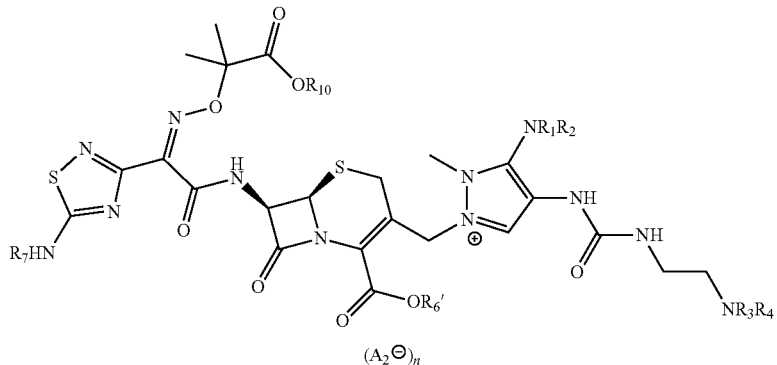

V wherein
R$_1$-R$_4$ and R$_{6'}$ are as defined above,
R$_7$ is hydrogen or an amino protecting group,
R$_{10}$ is an ester protecting group, preferably allyl, benzyl, tert-butyl, methyl, alkoxyalkyl or benzhydryl, most preferably tert-butyl, and
A$_2^\ominus$ is an anion, with the condition that n is zero when R$_{6'}$ is a negative charge, and
n is one when R$_{6'}$ is hydrogen,
which comprises the step of
reacting the compound of formula II with a compound of formula

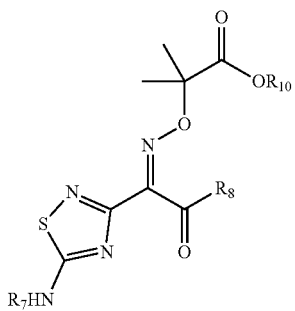

VI wherein R$_7$ and R$_{10}$ are as defined above,

R$_8$ is Cl or SR$_9$, wherein R$_9$ is C$_1$-C$_6$ straight or branched alkyl, C$_3$-C$_6$ cycloalkyl, or a substituted or unsubstituted mono- or bicyclic aryl or heteroaryl ring system of 5 to 12 atoms and where each monocyclic ring contains 0 to 3 hetero atoms, and each bicyclic ring contains 0 to 4 hetero atoms selected from N, O and S, and c) removing any protecting groups from the compound of formula V to produce a compound of formula I, d) if in the compound of formula I produced in step c) R$_{6'}$ is a negative charge and n is zero optionally treating the compound of formula I produced in step c) with an acid to produce a compound of formula I, wherein R$_{6'}$ is hydrogen and n is one, e) optionally exchanging the anion by a different anion in the compound of formula I produced in step d) or in the compound of formula I produced in step c) if R$_{6'}$ is hydrogen and n is one, wherein step c) comprises c1) selectively removing any triphenylmethyl groups from the compound of formula V to produce a compound of formula

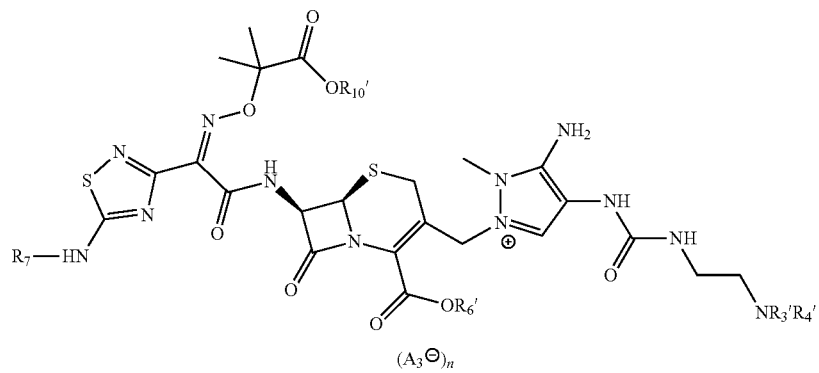

VII and c2) removing any remaining protecting groups of the compound of formula VII
wherein
$R_{3'}$, $R_{4'}$, $R_{6'}$, $R_{7'}$ and $R_{10'}$ are defined as $R_3$, $R_4$, $R_{6'}$, $R_7$ and $R_{10}$ before, respectively with the exception that $R_{3'}$, $R_{4'}$, $R_{7'}$ and $R_{10'}$ are not triphenylmethyl and if $R_3$ and/or $R_4$ and/or $R_7$ and/or $R_{10}$ are triphenylmethyl in the compound of formula V $R_{3'}$ and/or $R_{4'}$ and/or $R_{7'}$ and/or $R_{10'}$ are hydrogen in the compound of formula VII, respectively, and
$A_3^{\ominus}$ is an anion, with the condition that n is zero when $R_{6'}$ is a negative charge, and n is one when $R_{6'}$ is hydrogen.

In an even more preferred embodiment, the present invention refers to a method for preparing a compound of formula

I wherein
$R_{6'}$ is hydrogen or a negative charge, and
$A^{\ominus}$ is an anion, with the condition that n is zero when $R_{6'}$ is a negative charge, and n is one when $R_{6'}$ is hydrogen, comprising the steps of
a) preparing a compound of formula

II wherein
$R_1$ is triphenylmethyl and $R_2$ is hydrogen,
$R_3$ is a tert-butoxycarbonyl (Boc) group and $R_4$ is hydrogen,
$R_5$ is trimethylsilyl or hydrogen,
$R_6$ is trimethylsilyl, hydrogen or a negative charge, and
$A_1^{\ominus}$ is an anion, with the condition that n is zero when $R_6$ is a negative charge, and
n is one, when $R_6$ is trimethylsilyl or hydrogen, which comprises the steps of
a-i) reacting a compound of formula

III with a trimethylsilylating agent, optionally in presence of a catalyst, and
with iodotrimethylsilane,
a-ii) providing a compound of formula

IV wherein
$R_1$-$R_4$ are as defined above, and
optionally reacting the compound of formula IV with a trimethylsilylating agent,
a-iii) reacting the products of steps a-i) and a-ii),
a-iv) and optionally desilylating the product of step a-ii)

b) preparing a compound of formula

V

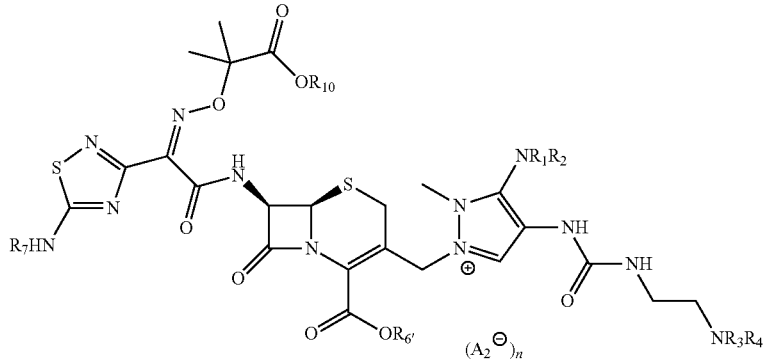

wherein
$R_1$-$R_4$ and $R_{6'}$ are as defined above,
$R_7$ is hydrogen,
$R_{10}$ is tert-butyl, and
$A_2^{\ominus}$ is an anion, with the condition that n is zero when $R_{6'}$ is a negative charge, and
n is one when $R_{6'}$ is hydrogen,
which comprises the step of
reacting the compound of formula II with a compound of formula

VI

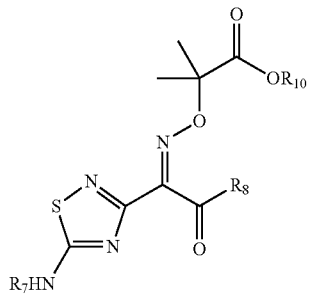

wherein $R_7$ and $R_{10}$ are as defined above, and
$R_8$ is Cl or

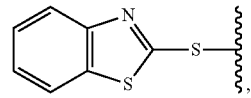

and c) removing any protecting groups from the compound of formula V to produce a compound of formula I, d) if in the compound of formula I produced in step c) $R_{6'}$ is a negative charge and n is zero optionally treating the compound of formula I produced in step c) with an acid to produce a compound of formula I, wherein $R_{6'}$ is hydrogen and n is one, e) optionally exchanging the anion by a different anion in the compound of formula produced in step d) or in the compound of formula I produced in step c) if $R_{6'}$ is hydrogen and n is one, wherein step c) comprises
c1) selectively removing the triphenylmethyl group from the compound of formula V to produce a compound of formula

VII

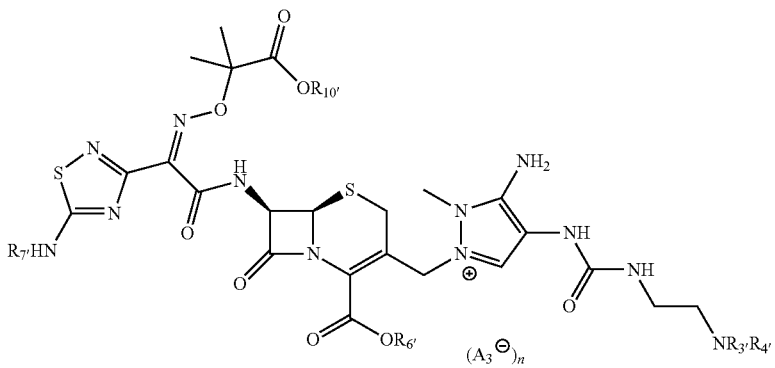

and
c2) removing any remaining protecting groups of the compound of formula VII wherein
$R_{3'}$, $R_{4'}$, $R_{6'}$, $R_{7'}$ and $R_{10'}$ are defined as $R_3$, $R_4$, $R_{6'}$, $R_7$ and $R_{10}$ before, and
$A_3^{\ominus}$ is an anion, with the condition that n is zero when $R_{6'}$ is a negative charge, and n is one when $R_{6'}$ is hydrogen.

In a particularly preferred embodiment, the present invention refers to a method for preparing a compound of formula

I

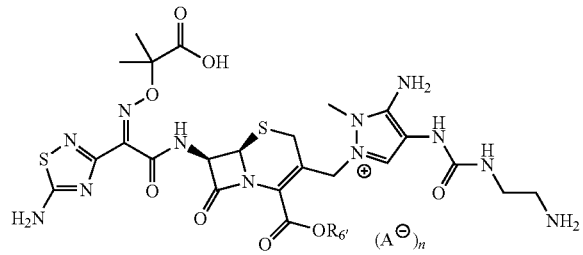

wherein
$R_{6'}$ is hydrogen and
$A^{\ominus}$ is hydrogen sulfate and n is one.
comprising the steps of
a) preparing a compound of formula

II

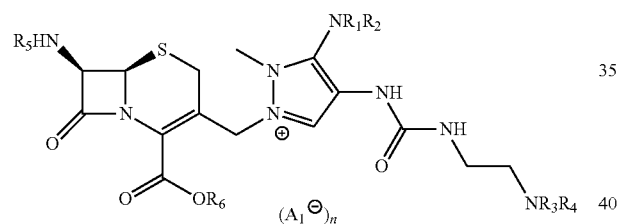

wherein
$R_1$ is triphenylmethyl and $R_2$ is hydrogen,
$R_3$ is a tert-butoxycarbonyl (Boc) group and $R_4$ is hydrogen,
$R_5$ is trimethylsilyl, $R_6$ is trimethylsilyl, and
$A_1^{\ominus}$ is iodide and n is one,
which comprises the steps of
a-i) reacting a compound of formula

III

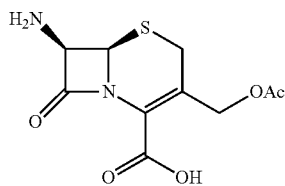

with a trimethylsilylating agent, optionally in presence of a catalyst, and with iodotrimethylsilane,
a-ii) providing a compound of formula

IV

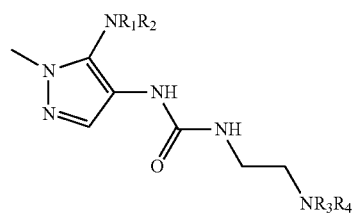

wherein
$R_1$-$R_4$ are as defined above, and
optionally reacting the compound of formula IV with a trimethylsilylating agent,
a-iii) reacting the products of steps a-i) and a-ii),
b) preparing a compound of formula

V

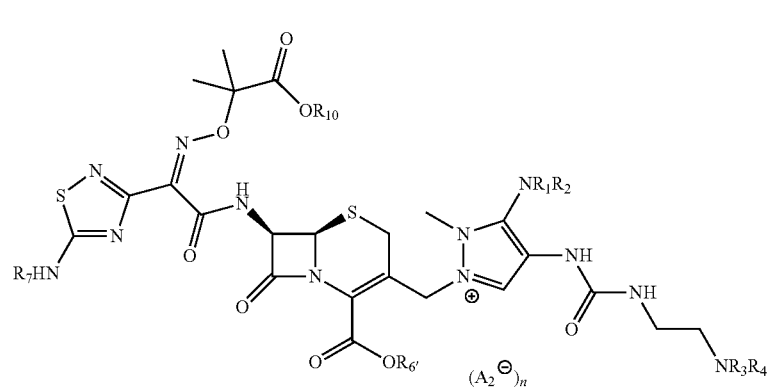

wherein
$R_1$-$R_4$ and $R_{6'}$ are as defined above,
$R_7$ is hydrogen,
$R_{10}$ is tert-butyl, and
$A_2^{\ominus}$ is trifluoroacetate and n is one, which comprises the step of
reacting the compound of formula II with a compound of formula

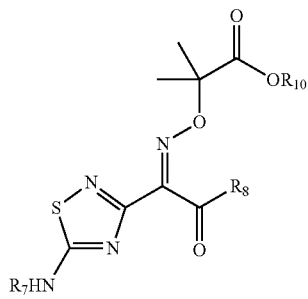

VI wherein $R_7$ and $R_{10}$ are as defined above, and $R_8$ is Cl or

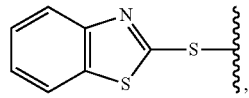

and
c) removing any protecting groups from the compound of formula V to produce a compound of formula I,
d) exchanging the anion by a different anion in the compound of formula I produced in step c),
wherein step c) comprises
c1) selectively removing the triphenylmethyl group from the compound of formula V to produce a compound of formula

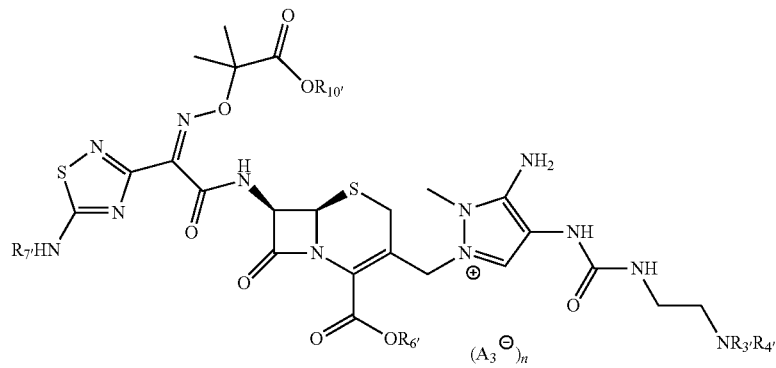

VII and
c2) removing any remaining protecting groups of the compound of formula VII
wherein
$R_{3'}$, $R_{4'}$, $R_{6'}$, $R_{7'}$ and $R_{10'}$ are defined as $R_3$, $R_4$, $R_{6'}$, $R_7$ and $R_{10}$ before, and
$A_3^\ominus$ is formate and n is one.

In one embodiment, step c1) is conducted by reacting the compound of formula V, wherein $R_1$ is triphenylmethyl and $R_2$ is hydrogen, with an acid in a protic solvent.

Suitable acids to be used in the present invention are, e.g., HCl, HCOOH, $CH_3COOH$, trifluoroacetic acid (TFA), $H_2SO_4$, sulfamic acid and $H_3PO_4$. Suitable protic solvents to be used in the present invention are, e.g., methanol, ethanol, isopropanol, butanol, 2-butanol and 2,2,2-trifluoroethanol. $A_3^\ominus$ in the compound of formula VII is preferably an anion deriving from the acid preferably used in step c1) of the present invention and $R_{6'}$ is hydrogen and n is one. It is further preferred that $R_{3'}$ is tert-butyloxycarbonyl, $R_{4'}$ and $R_{7'}$ are hydrogen and $R_{10'}$ is tert-butyl in the compound of formula VII.

Preferably step c1) is conducted by reacting the compound of formula V, wherein $R_1$ is triphenylmethyl and $R_2$ is hydrogen, with an acid in a protic solvent, wherein the acid in a protic solvent is selected from the group of formic acid in ethanol, hydrochloric acid in acetone-water mixture, acetic acid in ethanol, hydrochloric acid in ethanol, and sulfamic acid in ethanol. More preferably formic acid in ethanol (e.g. at a 1:1 volume per volume ratio at −10 to −15° C.) is used in step c1) of the present invention for selectively removing all triphenylmethyl groups, from the compound of formula V to form a compound of formula VII, wherein $R_{6'}$ is hydrogen, n is one and $A_3^\ominus$ is formate.

The present inventors observed a severe baseline increase by RP-HPLC detection after the alkylation step (see step a)) which could not be separated by prep. RP-HPLC, normal phase silica column or alox columns. It was, however, found that after acylation (step b)) and selective cleavage of the triphenylmethyl (trityl) protecting group a precipitate was yielded in an aqueous work-up. This in-homogenous mixture of compounds was responsible for the baseline increase. The precipitate could be filtered off with a pressure filter, yielding the compound of formula VII in 55-75% purity (by NMR). After removal of the insoluble impurities, the compound of formula VII in amorphous form can be converted into a crystalline form by reslurrying it in acetonitrile, The reaction mixture of step c1) is thus preferably subjected to an aqueous workup and insoluble precipitate is removed before any remaining protective groups of the compound of formula VII are removed in a step c2) (wherein preferably an acid is used) to produce a compound of formula I. The reaction mixture is therefore mixed with water (preferably at ≤5° C.) and the precipitate is removed, e.g. by filtering it off. Thereby, insoluble impurities are removed. The remaining aqueous solution can be further purified by solid phase extraction (e.g. by loading on a RP-silica column, washing the column with a suitable medium, such as water, and eluting the compound of formula VII with a suitable solvent, such as ethanol).

In a preferred embodiment of the present invention, compound VII is isolated after step c1) prior to performing the deprotection of step c2). After purification by e.g. solid phase extraction, compound VII can be e.g. isolated by azeotropic distillation of the solvent.

In general, a temperature of ≤−10° C. or ≤−15° C. is preferred for reacting the compound of formula V, wherein at $R_1$ is triphenylmethyl and $R_2$ is hydrogen, with the acid in the protic solvent in step c1). The reaction with the acid in the protic solvent is preferably conducted for 5-16 hours, preferably 7-12 hours.

Preferably, in the present invention $H_2SO_4$ is used in step c2), or in step c) in general (if deprotection is not stepwise such as in steps c1) and c2)) to produce a compound of formula I, wherein $A^\ominus$ is $HSO_4^-$, $R_{6'}$ is hydrogen and n is one and a solvent is used, which is selected from one or a combination of two or more solvents of the group consisting of 2,2,2-trifluoroethanol, methylisobutylketon (optionally diluted with water), ethyl acetate, acetic acid, methylethylketon and dimethylcarbonate or acetonitrile.

More preferably 2,2,2-trifluoroethanol, methylisobutylketon (MIBK), or a mixture of 2-ethyl acetate and acetic acid (HOAc) are used as solvent in step c2), or in step c) in general and most preferably, 2,2,2-trifluoroethanol is used in step c2), or in step c) in general. Preferably the reaction temperature in step c2), or in step c) in general is ≤5° C. (e.g. about 0° C.).

It is preferred to use 3-14, more preferably 4-12, such as 6 equivalents (compared to the employed amount of the compound of formula V or VII) of $H_2SO_4$ as the acid in step c2) or in step c) in general.

In the global deprotection step c2) (or c) in general if deprotection is not stepwise) typically a precipitate forms during deprotection that can be collected. The method for preparing the compound of formula I thus preferably comprises a step of collecting the compound of formula I as a precipitate.

The present invention also relates to a method for preparing a compound of formula I as defined above from a compound of formula V as defined above comprising a step c) as defined above or from a compound of formula VII as defined above comprising a step c2) as defined above.

The present invention also relates to a method for preparing a compound of formula VII as defined above from a compound of formula V as defined above comprising a step c1) as defined above.

A compound of formula VII (wherein it is preferred that $R_{3'}$ is tert-butyloxycarbonyl and $R_{4'}$ and $R_{7'}$ are hydrogen and wherein it is further preferred that $R_{10'}$ is tert-butyl) in crystalline form is obtainable by reslurrying the compound of formula VII in amorphous form in acetonitrile.

The present invention also relates to a method for preparing a compound of formula V as defined above from a compound of formula II as defined above and a compound of formula VI as defined above comprising a step b) as defined above. Preferably, the compound of formula V is prepared from the compounds of formulae III, IV and VI as defined above. In a preferred embodiment of the method for preparing a compound of formula V, the compound of formula II is thus prepared from the compounds of formula III and IV as defined above by a method comprising a step a) as defined above. More preferably, the compound of formula II is not isolated from the reaction mixture of step a) before it is reacted with the compound of formula VI in step b) in this case.

The present invention also relates to a method for preparing a compound of formula II as defined above from a compound of formula II as defined above and a compound of formula IV as defined above comprising steps a-i) to a-iii) and optionally a-iv) as defined above.

The present invention further also relates to a compound of formula

VII

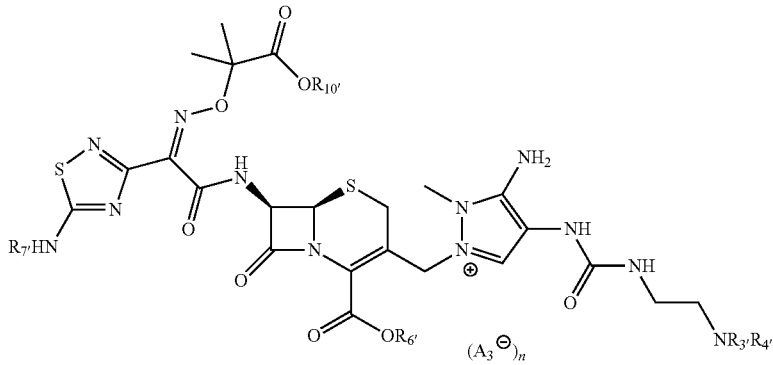

wherein $R_{3'}$, $R_{4'}$, $R_{6'}$, $R_{7'}$ and $R_{10'}$, and $A_3^\ominus$ and n are as defined above. More preferably, in the compound of formula VII $R_{3'}$ is tert-butyloxycarbonyl and $R_{4'}$ and $R_{7'}$ are hydrogen. The compound of formula VII is preferably crystalline. A compound of formula VII in crystalline form is obtainable by reslurrying the compound of formula VII in amorphous form in acetonitrile.

In a most preferred embodiment, the compound of formula VII is crystalline and $R_3$ is tert-butyloxycarbonyl and $R_{4'}$ and $R_{7'}$ are hydrogen. $R_{10'}$ is preferably tert-butyl in the compound of formula VII. In one embodiment, $A_3^\ominus$ is, e.g., formate in the compound of formula VII, $R_{6'}$ is hydrogen and n is one in the compound of formula VII. A most preferred compound of formula VII is thus, as illustrated below,

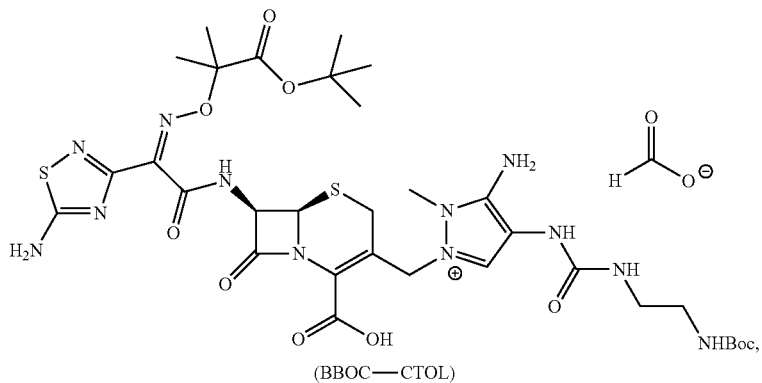

(BBOC—CTOL)

a compound of formula VII, wherein $R_3$ is a tert-butoxycarbonyl (Boc) group and $R_4$ is hydrogen,
$R_{6'}$ is hydrogen,
$R_7$ is hydrogen,
$R_{10}$ is tert-butyl, and
$A_3^{\ominus}$ is formate and n is one.

In a preferred embodiment, the above compound BBOC-CTOL is in crystalline form, more preferably in a crystalline form defined by an X-Ray powder diffraction (XRPD) pattern having diffractions at angles (2 theta±0.2) of
4.9,
6.7,
7.2,
12.9,
13.4;
more preferably defined by an XRPD pattern having diffractions at angles (2 theta±0.2) of
4.9,
6.7,
7.2,
7.7,
8.0,
9.3,
10.1,
11.8,
12.9,
13.4,
15.1.

If nothing else is stated, XRPD data is obtained with a diffractometer using the following settings:

| Measurement Temperature [° C.] | 25.00 |
|---|---|
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 45 kV. |

The present invention further also relates to a compound of formula

V

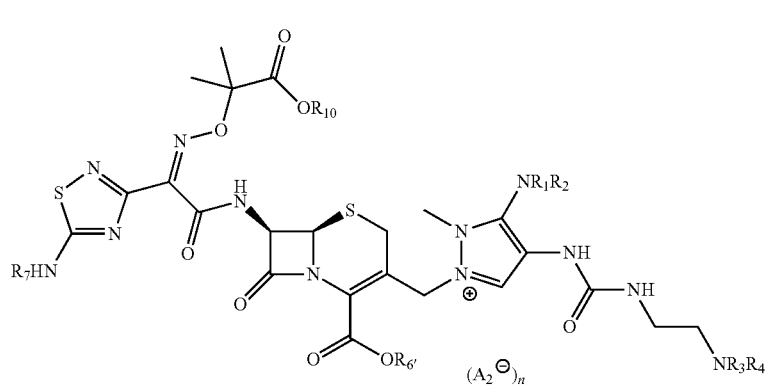

wherein $R_1$-$R_4$, $R_{6'}$, $R_7$, $R_{10}$, and $A_2^\ominus$ and n are as defined above. A particularly preferred compound of formula V is illustrated below,

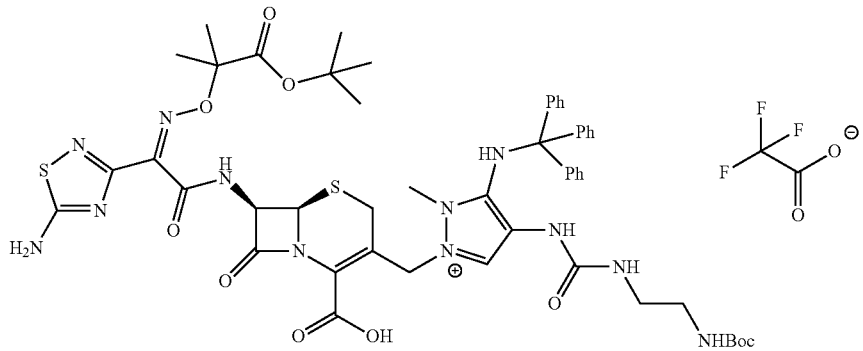 [SMILES: Cn1c(NC(c2ccccc2)(c2ccccc2)c2ccccc2)c(NC(=O)NCCNC(=O)OC(C)(C)C)c[n+]1CC1=C(C(=O)O)N2C(=O)[C@@H](NC(=O)/C(=N\OC(C)(C)C(=O)OC(C)(C)C)c3nsc(N)n3)[C@H]2SC1 ; O=C([O-])C(F)(F)F]

i.e. a compound of formula V, wherein $R_1$ is a triphenylmethyl group and $R_2$ is hydrogen,
$R_3$ is a tert-butoxycarbonyl (Boc) group and $R_4$ is hydrogen,
$R_{6'}$ is hydrogen,
$R_7$ is hydrogen,
$R_{10}$ is tert-butyl, and
$A_2^\ominus$ is trifluoroacetate and n is one.

The present invention further also relates to a compound of formula

II

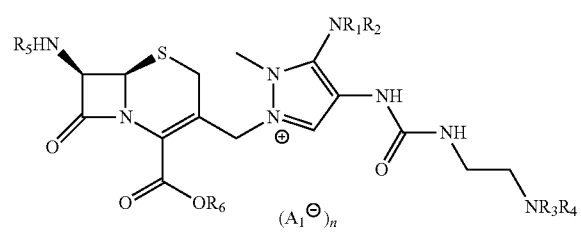

wherein $R_1$-$R_6$ and $A_1^\ominus$ and n are as defined above. Particularly preferred compounds of formula II are illustrated below,

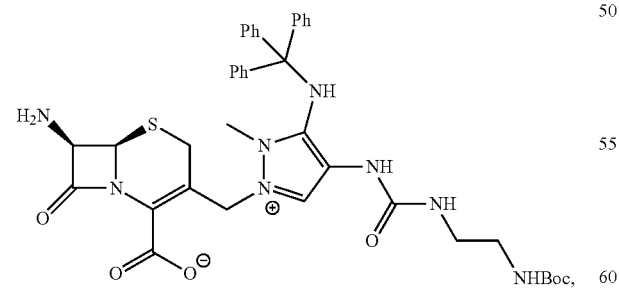

i.e. a compound of formula II, wherein
R is a triphenylmethyl group and $R_2$ is hydrogen,
R is a tert-butoxycarbonyl (Boc) group and $R_4$ is hydrogen,
$R_5$ is hydrogen,
$R_6$ is a negative charge and n is zero;

and

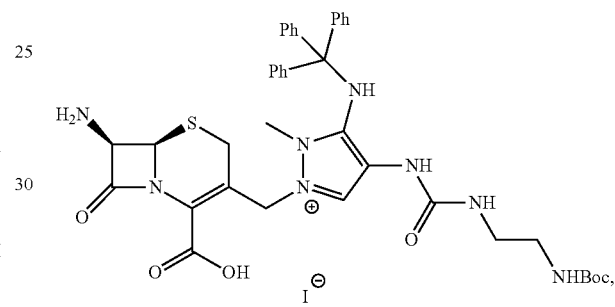

i.e. a compound of formula II, wherein
$R_1$ is a triphenylmethyl group and $R_2$ is hydrogen,
$R_3$ is a tert-butoxycarbonyl (Boc) group and $R_4$ is hydrogen,
$R_5$ is hydrogen,
$R_6$ is hydrogen, and
$A_1^\ominus$ is iodide and n is one.

The present invention further also relates to a compound of formula

VI

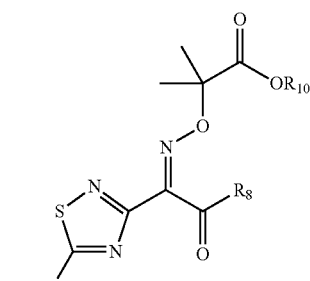

wherein $R_7$, $R_8$ and $R_{10}$ are as defined above. Particularly preferred compounds of formula VI include e.g.
a compound of formula VI, wherein
$R_7$ is hydrogen or an amino protecting group,
$R_{10}$ is tert-butyl, and
$R_8$ is Cl;

and
a compound of formula VI, wherein
R₇ is hydrogen or an amino protecting group,
R₁₀ is tert-butyl, and
R₈ is

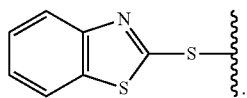

Particularly preferred compounds of formula VI thus include the following compounds:

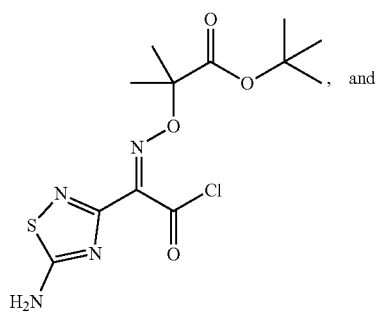, and

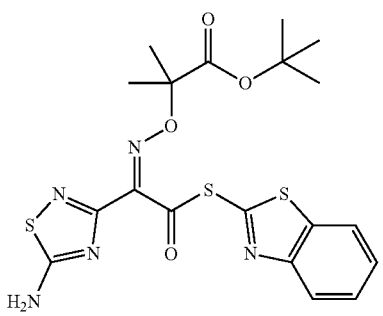

Preferred compounds of formula VI thus also include the following compounds:

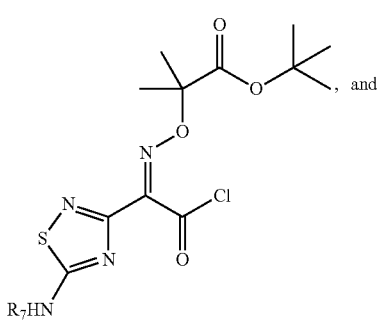, and

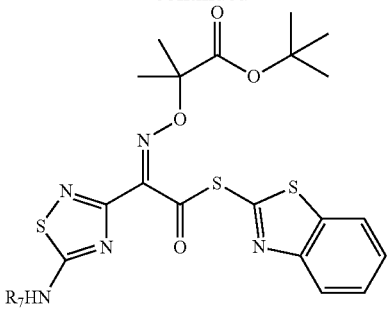

wherein R₇ an amino protecting group, which is preferably selected from the group consisting of triphenylmethyl (trityl, Tr), benzyl, allyl, carbamate forming protecting groups such as benzyloxycarbonyl (Cbz), allyloxycarbonyl (Aloc), 9-fluorenylmethoxycarbonyl (Fmoc), tert-butoxycarbonyl (Boc), 2-(trimethylsilyl)ethoxycarbonyl (Teoc), 2,2,2-trichloroethoxycarbonyl (Troc), silyl groups (e.g. TMS), STABASE (—Si(CH₃)₂—CH₂C₂—(CH₃)₂Si—), Benzostabase, and trazinanone forming protecting groups. More preferably, the amino protecting group is selected from the group consisting of carbamate-forming protecting groups. More preferably, the amino protecting group is selected from the group consisting of benzyloxycarbonyl (Cbz), allyloxycarbonyl (Aloc), 9-fluorenylmethoxycarbonyl (Fmoc), tert-butoxycarbonyl (Boc), 2-(trimethylsilyl)ethoxycarbonyl (Teoc) and 2,2,2-trichloroethoxycarbonyl (Troc). Even more preferably, the amino protecting group is tert-butoxycarbonyl (Boc).

The following examples are illustrative without restricting the scope of protection. If in the examples and comparative examples a process detail is not explicitly described, a skilled person can easily find such detail according to the general practice in the art.

EXAMPLE 1

2-(((6R,7R)-7-((Z)-2-(5-amino-1,2,4-thiadiazol-3-yl)-2-(((1-(tert-butoxy)-2-methyl-1-oxopropan-2-yl)oxy)imino)acetamido)-2-carboxy-8-oxo-5-thia-1-azabicyclo[4.2.0]-oct-2-en-3-yl)methyl)-4-(3-(2((tert-butoxycarbonyl)amino)ethyl)ureido)-1-methyl-5-(trityl-amino)-1H-pyrazol-2-ium 2,2,2-trifluoroacetate 7-ACA (30.0 g, 110.8 mmol) was dissolved in 570 mL CH₂Cl₂ and heated to 60° C. HMDS (2-3 mL) and TMJS (100 µL) were added and the solution was purged with N₂. Within 20 min the remaining HMDS (68.39 mL, 52.35 g, 3 eq) was added dropwise and the reaction mixture was further refluxed for 4 hours while purging the solution with N₂. Then the solution was cooled to RT and evaporated to dryness. The residual solid was dissolved with 120 mL CH₂Cl₂ and cooled to −5° C. TMJS (26.46 g, 132.22 mmol, 1.2 eq) was added dropwise over 20 min and the reaction mixture was stirred at −5° C. over night (Solution A).

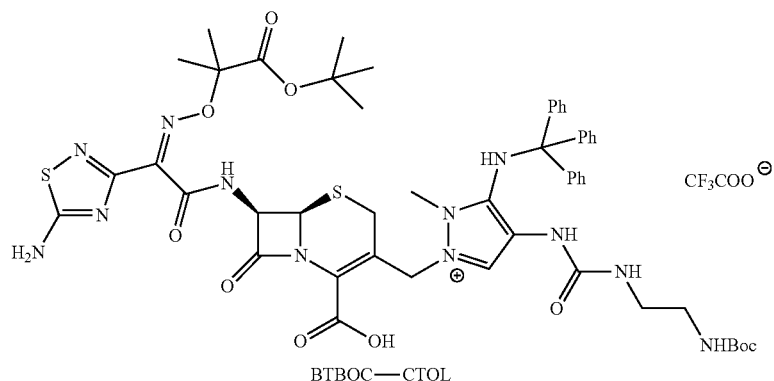

BTBOC—CTOL tert-Butyl (2-(3-(1-methyl-5-(tritylamino)-1H-pyrazol-4-yl)ureido)ethyl)carbamate (T-BAMPU, 71.5 g, 132.22 mmol, 1.2 eq) was dissolved in 240 mL dry NMP at 45-50° C. Then the solution was cooled to RT and proton Sponge® (23.61 g, 110.18 mmoL, 1.0 eq) and BSA (26.90 g, 132.22 mmoL, 1.2 eq) were added. After stirring the reaction mixture for 1 hour, solution A (see above) was added dropwise within 10 min. The remaining solution was stirred for 22 hours at room temperature. After cooling the reaction mixture to 0° C., (Z)-tert-butyl 2-(((1-(5-amino-1,2,4-thiadiazol-3-yl)-2-chloro-2-oxoethylidene)amino)oxy)-2-methy propanoate (BATDPO-CL, 40.4 g, 115.69 mmol, 1.05 eq) was added in small portions, whereby the reaction temperature remained below 5° C. The solution was stirred at 0-5° C. for 4 hours and subsequently filtered to remove the protonated proton Sponge®. The reaction mixture was quenched with an aqueous NaHCO₃ solution (5%, 500 mL) and the aqueous phase was extracted with CH₂Cl₂ (2×500 mL). The combined organic phases were subsequently washed with half saturated NH₄Cl solution (500 mL), then H₂O (500 mL) and dried over Na₂SO₄. The remaining solution was concentrated under reduced pressure to ~400 mL and then was added slowly to a stirred aqueous NaTFA solution (30 g/3 L, pH=8) under ice cooling. The orange precipitate was filtered off, washed with cold water (500 mL) and cyclohexane (200 mL). The residual solid (290 g, ~10 w/w % BTBOC-CTOL=29 g BTBOC-CTOL) was stored at −20° C. ESI-MS: m/z 1065.4 (M+)

EXAMPLE 2

5-amino-2-(((6R,7R)-7-((Z)-2-(5-amino-1,2,4-thiadiazol-3-yl)-2-(((1-(tert-butoxy)-2-methyl-1-oxopropan-2-yl)oxy)imino)acetamido)-2-carboxy-8-oxo-5-thia-1-aza-bicyclo[4.2.0]oct-2-en-3-yl)methyl)-4-(3-(2-((tert-butoxycarbonyl)amino)ethyl)ureido)-1-methyl-1H-pyrazol-2-ium formate

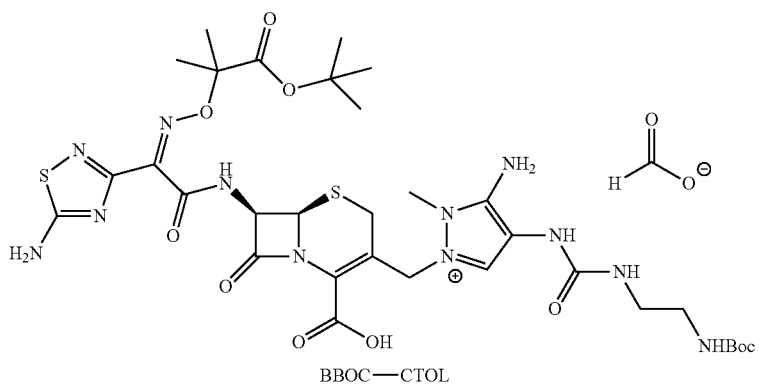

BBOC—CTOL

Crude TBOC-CTOL (~10 w/w %) from example 1 (70 g) was dissolved in dry ethanol (150 mL) and conc. formic acid (150 mL) and stirred at −15° C. over night. Then the reaction mixture was poured slowly into ice cold water (2.5 L), further stirred for 2 hours and celite was added. The precipitate was filtered off, washed with water and the remaining aqueous solution was loaded on a RP-silica column (solid phase extraction). The column was washed with water and then BBOC-CTOL was eluted with ethanol (100 mL). The resulting solution was azeotropically dried with toluene and subsequently with $Na_2SO_4$ to remove traces of water. Then pentane was added slowly to the mixture, resulting in the formation of a white solid (BBOC-CTOL, Yield: 4.38 g). Reslurrying the solid for 2 days in acetonitrile yielded crystalline BBOC-CTOL. H-NMR (400 MHz, D2): δ 8.10 (s, 1H, formate), 7.94 (s, 1H, CH), 5.86 (d, J=4.9 Hz, 1H, CH), 5.28 (d, J=15.4 Hz, 1H, $CH_2$), 5.12 (d, J=4.9 Hz, 1H, CH), 5.00 (d, J=14.7 Hz, 1H, $CH_2$), 3.75 (s, 3H, CH3), 3.36 (d, J=17.6 Hz, 1H, $CH_2$), 3.27-3.10 (m, 5H, $CH_2$), 1.57 (s, 3H, $CH_3$), 1.56 (s, 3H, $CH_3$), 1.46 (s, 9H, $CH_3$), 1.44 (s, 9H, $CH_3$). ESI-MS: m/z 823.3 (M+)

EXAMPLE 3

5-amino-2-((((6R,7R)-7-((Z)-2-(5-amino-1,2,4-thiadiazol-3-yl)-2-(((2-carboxypropan-2-yl)oxy)imino)acetamido)-2-carboxy-8-oxo-5-thia-1-azabicyclo[4.2.0]oct-2-en-3-yl)methyl)-4-(3-(2-aminoethyl)ureido)-1-methyl-1H-pyrazol-2-ium hydrogensulfate BBOC-CTOL (21.5 g, 55 w/w %) was dissolved in 300 mL trifluoroethanol and the mixture was cooled to 0° C. using an ice-bath. A solution of conc. $H_2SO_4$ (10 ml) in 50 mL trifluoroethanol was added and the reaction was stirred at rt for 2 hours. A white solid started to precipitate, which was filtered off, the residue was washed with trifluoroethanol and suction dried over $N_2$. The resulting solid was dissolved in water and filtered over a pad of LiChroprep® RP-18, eluting with a gradient from 1.5 to 3% ethanol in water. The resulting solution was concentrated under reduced pressure to ~500 ml and isopropanol (2 L) was added slowly to the solution, allowing the precipitation of ceftolozane sulfate (Yield: 5.1 g). $^1$H-NMR (400 MHz, $D_2O$): δ7.89 (s, 1H, CH), 5.85 (d, J=4.8 Hz, 1H, CH), 5.23 (d, J=4.8 Hz, 1H, CH), 5.19 (d, J=14.7 Hz, 1H, $CH_2$), 4.96 (d, J=14.7 Hz, 1H, $CH_2$), 3.70 (s, 3H, $CH_3$), 3.47 (t, J=5.8 Hz, 1H, $CH_2$), 3.45 (d, J=17.5 Hz, 1H, $CH_2$), 3.21 (d, J=17.8 Hz, 1H, $CH_2$), 3.13 (t, J=5.7 Hz, 1H, $CH_2$), 1.52 (s, 3H, $CH_3$), 1.51 (s, 3H, $CH_3$); ESI-MS: m/z 667.2 (M$^+$)

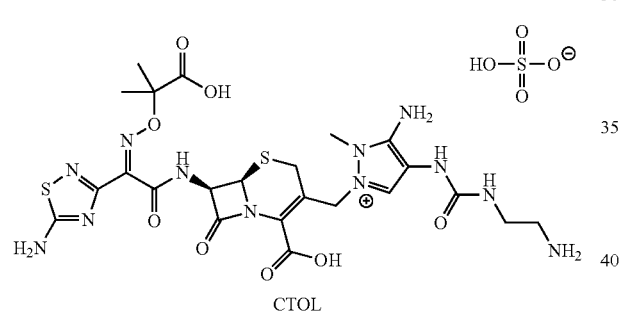

CTOL

EXAMPLE 4

For global deprotection different conditions were tested:

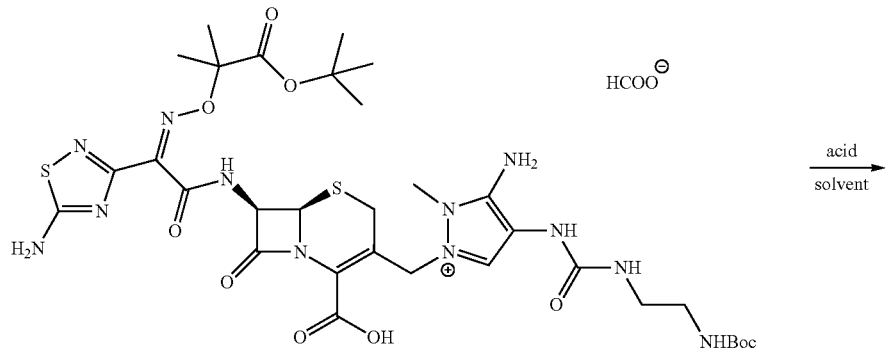

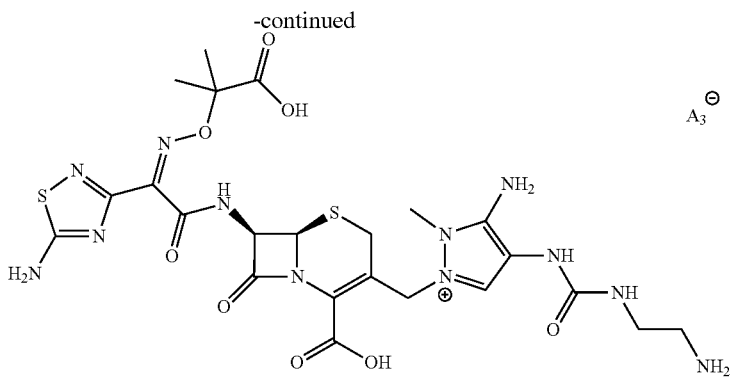

| experiment | acid | solvent(s) | Product formed | appearance |
|---|---|---|---|---|
| 1 | H2SO4 (6 eq.) | HOAc | x | sticky precipitate |
| 2 | H2SO4 (6 eq.) | Acetonitrile | (x) | sticky suspension |
| 3 | H2SO4 (6 eq.) | MeOH | | solution |
| 4 | H2SO4 (6 eq.) | EtOH | | sticky precipitate |
| 5 | H2SO4 (6 eq.) | EtOAc | x | suspension |
| 6 | H2SO4 (6 eq.) | Diethylcarbonate | | sticky suspension |
| 7 | H2SO4 (6 eq.) | DMAc | | solution |
| 8 | H2SO4 (6 eq.) | 2-Butanone | x | suspension |
| 9 | H2SO4 (6 eq.) | MIBK | x | suspension |
| 10 | H2SO4 (6 eq.) | CH2Cl2 | | sticky suspension |
| 11 | H2SO4 (6 eq.) | Diethylcarbonate | (x) | sticky precipitate |
| 12 | H2SO4 (6 eq.) | 2,2,2-Trifluorethanol | x | suspension |
| 13 | H2SO4 (6 eq.) | Isopropanol (ISO) | | |
| 14 | H2SO4 (6 eq.) | ISO/HOAc (3/1) | | sticky suspension |
| 15 | H2SO4 (12 eq.) | MIBK/H2O | x | biphasic mixture |
| 17 | H2SO4 (6 eq.) | EtOAc/HOAc (1/1) | x | sticky suspension |
| 18 | H2SO4 (6 eq.) | MIBK | x | suspension |
| 19 | H2SO4 (6 eq.) | MIBK (more diluted) | x | suspension |
| 20 | H2SO4 (6 eq.) | EtOAc/HOAc (1/1) | x | suspension |
| 21 | H2SO4 (6 eq.) | EtOAc (double dil.) | x | suspension |
| 22 | H2SO4 (6 eq.) | EtOAc/HOAc (6/1) | x | suspension |
| 23 | H2SO4 (18 eq.) | MIBK | (x) | decomposition |
| 24 | H2SO4 (6 eq.) | MIBK | (x) | incomplete conv. |
| 25 | TFA | Anisole/CH2Cl2 | x | suspension |

The best yield (80%) and fastest reaction was obtained with $H_2SO_4$ in trifluoroethanol (example 12). The yield of the reaction with TFA in anisole/$CH_2Cl_2$ was 70%.

EXAMPLE 5

(Z)-tert-butyl 2-(((1-(5-amino-1,2,4-thiadiazol-3-yl)-2-chloro-2-oxoethylidene)-amino)oxy)-2-methylpropanoate

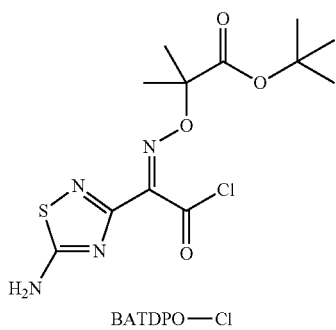

BATDPO—Cl

BATDPO ((Z)-2-(5-amino-1,2,4-thiadiazol-3-yl)-2-(((1-(tert-butoxy)-2-methyl-1-oxopropan-2-yl)oxy)imino)acetic acid) (80 g, 0.242 mol, 1 eq) was suspended in 1080 mL $CH_2Cl_2$ and was cooled to −12° C. DMF (932 μL, 0.05 eq) and oxalyl chloride (24.92 mL, 0.290 mmol, 1.2 eq) was added within 5 min. The reaction mixture was poured into 6 L diisopropylether after stirring for 75 min. The suspension was further stirred for 3 hours at 0° C., filtered and dried under vacuum to yield 84.4 g of BATDPO-Cl. ((Z)-tert-butyl 2-(((1-(5-amino-1,2,4-thiadiazol-3-yl)-2-chloro-2-oxoethylidene)amino)oxy)-2-methylpropanoate). H-NMR (400 MHz, THF-D8): δ7.59 (bs, 2H, $NH_2$), 1.52 (s, 6H, $CH_3$), 1.42 (s, 9H, $CH_3$)

EXAMPLE 6

(Z)-tert-butyl 2-(((1-(5-amino-1,2,4-thiadiazol-3-YL)-2-(benzo[D]thiazol-2-ylthio)-2-oxoethylidene)amino)oxy)-2-methylpropanoate

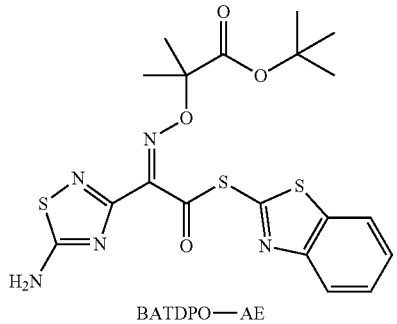

BATDPO—AE

BATDPO ((Z)-2-(5-amino-1,2,4-thiadiazol-3-yl)-2-(((1-(tert-butoxy)-2-methy-1-oxopropan-2-yl)oxy)imino)acetic acid) (30 g, 90.8 mmol, 1 eq), 2,2'-dithiobis(benzothiazole) (36.2 g, 108.9 mmol, 1.2 eq) and triphenylphosphine (29.7 g, 113.2 mmol, 1.2 eq) was suspended in 450 mL $CH_2Cl_2$ and cooled to 0° C. Triethylamine (15.15 mL, 109.3 mmol, 1.2 eq) was added within 2 min. The reaction was stirred for 30 min at room temperature, cooled to 0° C. using an ice-bath and the crystalline solid was filtered off after 60 min to yield 30.0 g (Z)-tert-butyl 2-(((1-(5-amino-1,2,4-thiadiazol-3-yl)-2-(benzo[d]thiazol-2-ylthio)-2-oxoethylidene)amino)-oxy)-2-methylpropanoate. $^1$H-NMR (400 MHz, THF-D8): δ 8.07 (d, J=7.9 Hz, 1H, CH) 8.02 (d, J=8.1 Hz, 1H, CH) 7.60 (bs, 2H, $NH_2$), 7.53 (pseudo dt, J=7.6, 1.2 Hz, 1H, CH), 7.47 (pseudo dt, J=7.7, 1.0 Hz, 1H, CH), 1.57 (s, 6H, $CH_3$), 1.49 (s, 9H, $CH_3$)

EXAMPLE 7

5-amino-2-(((6R,7R)-7-((Z)-2-(5-amino-1,2,4-thiadiazol-3-yl)-2-(((1-(tert-butoxy)-2-methyl-1-oxopropan-2-yl)oxy)imino)acetamido)-2-carboxy-8-oxo-5-thia-aza-bicyclo[4.2.0]oct-2-en-3-yl)methy)-4-(3(2-((tert-butoxycarbonyl)amino)ethyl)ureido)-1-methyl-1H-pyrazol-2-ium acetate solution was stirred at 0-5° C. for 2 hours and subsequently filtered to remove the protonated proton Sponge®. The reaction mixture was quenched with an aqueous $NaHCO_3$ solution (5%, 10 mL) and the aqueous phase was extracted with $CH_2Cl_2$ (2×20 mL). The combined organic phases were subsequently washed twice with half saturated $NH_4Cl$ solution (10 mL), then $H_2O$ (10 mL) and dried over $Na_2SO_4$. The remaining solution was concentrated under reduced pressure to 30 mL and precipitate was formed after the addition of cyclohexane (100 mL). The residual solid was further purified by using a RP-HPLC (Gradient elution with $CH_3COONH_4/CH_3CN$, pH=7) to yield 110 mg BBOC-CTOL.

$^1$H-NMR (400 MHz, D2O): δ 7.94 (s, 1H, CH), 5.86 (d, J=4.9 Hz, 1H, CH), 5.28 (d, J=15.4 Hz, 1H, $CH_2$), 5.12 (d, J=4.9 Hz, 1H, CH), 5.00 (d, J=14.7 Hz, 1H, $CH_2$), 3.75 (s, 3H, CH3), 3.36 (d, J=17.6 Hz, 1H, $CH_2$), 3.27-3.10 (m, 5H, $CH_2$), 1.96 (s, 3H, acetate) 1.57 (s, 3H, $CH_3$), 1.56 (s, 3H, $CH_3$), 1.46 (s, 9H, $CH_3$), 1.44 (s, 9H, $CH_3$); ES-MS: m/z 823.3 (M+)

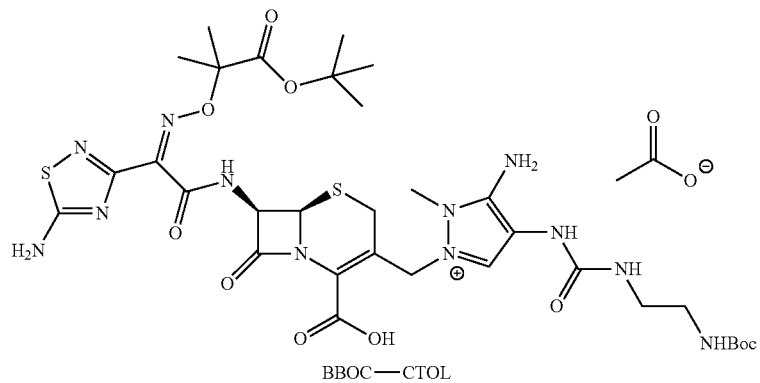

BBOC—CTOL

7-ACA (20.0 g, 73.45 mmol) was dissolved in 380 mL $CH_2Cl_2$ and heated to 60° C. HMDS (2 mL) and TMJS (20 µL) were added and the solution was purged with $N_2$. Within 20 min the remaining HMDS (Σ 45.6 mL, 35.6 g, 220.36 mmol, 3 eq) was added dropwise and the reaction mixture was further refluxed for 6 hours while purging the solution with $N_2$. Then the solution was cooled to RT and evaporated to dryness. The residual solid was dissolved with 80 mL $CH_2Cl_2$ (c=0.5 mmol/g) (Solution A).

Solution A (5 g, 2.50 mmol, bissilylated 7-ACA) cooled to -5° C. and TMJS (600 mg, 3 mmol, 1.2 eq) was added slowly. The reaction mixture was stirred at -50° C. overnight (Solution B). Tert-butyl (2-(3-(5-amino-1-methy-1H-pyrazol-4-yl)ureido)ethyl)carbamate (BAMPU) (895 mg, 3.0 mmol, 1.2 eq) was dissolved in 2.5 mL dry NMP and proton Sponge® (536 mg, 2.5 mmoL, 1.0 eq) and BSA (1.36 mL, 1.13 g, 5.55 mmoL, 2.2 eq) were added. After stirring the reaction mixture for 2 hour, solution B (see above) was added slowly. The remaining solution was stirred for 22 hours at room temperature. After cooling the reaction mixture to 0° C., proton Sponge® (589 mg, 2.75 mmoL, 1.1 eq) and BATDPO-CL (916 mg, 2.63 mmol, 1.05 eq) was added, whereby the reaction temperature remained below 5° C. The

EXAMPLE 8

X-Ray Powder Diffraction Spectrum of BBOC-CTOL

A sample of the crystalline BBOC-CTOL obtained in Example 2 was submitted to X-Ray powder diffraction (XRD), using a PANalytical X'Pert$^3$ X-ray diffractometer with the following measurement configuration:

| | |
|---|---|
| Measurement Temperature [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 45 kV. |

The following Table 1 shows the peak list of the XRD spectrum of BBOC-CTOL obtained in Example 2.

TABLE 1

| Pos. [°2Th.] ± 0.2 | Rel. Int. [%] |
|---|---|
| 4.9 | 100 |
| 6.7 | 40 |
| 7.2 | 20 |
| 7.6 | 14 |
| 8.0 | 17 |
| 9.3 | 11 |
| 10.1 | 9 |
| 11.8 | 11 |
| 12.9 | 61 |
| 13.4 | 29 |
| 15.1 | 21 |

COMPARATIVE EXAMPLE

WO 2014/152763 was repeated:

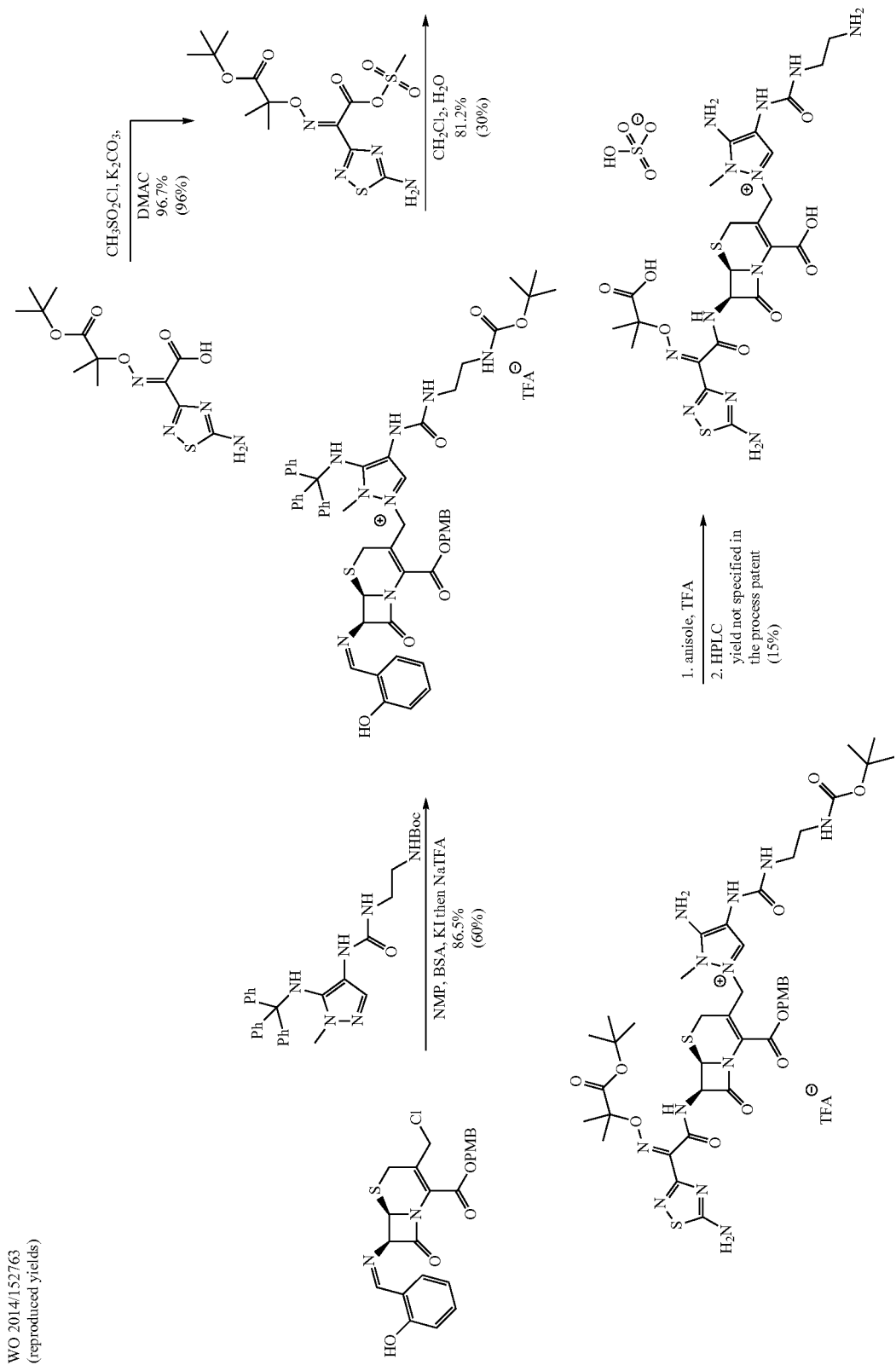

The yield for the 7-side chain coupling was considerably lower compared to what is indicated in WO 2014/152763. The yield for the global deprotection step (not indicated in WO 2014/152763) was very low (~15%).

The invention claimed is:

1. A method for preparing a compound of formula

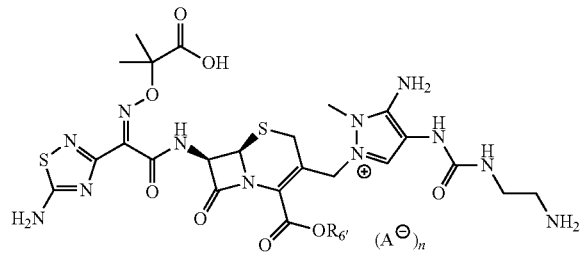

I wherein $R_{6'}$ is hydrogen or a negative charge, and $A^{\ominus}$ an anion, with the condition that n is zero when $R_{6'}$ is a negative charge, and n is one when $R_{6'}$ is hydrogen, comprising the steps of a) preparing a compound of formula

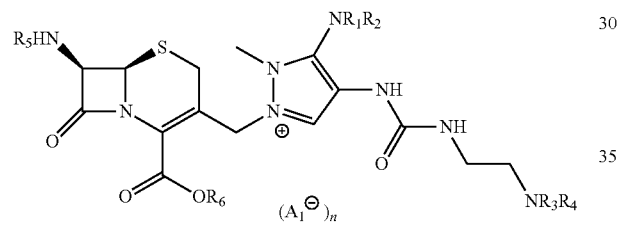

II wherein
- $R_1$, $R_2$, $R_3$ and $R_4$ are independently an amino protecting group or hydrogen with the condition that $R_4$ is not hydrogen if $R_3$ is hydrogen, or $R_1$ and $R_2$, and/or $R_3$ and $R_4$ are bound together by a cyclic amino protecting group,
- $R_5$ is trialkylsilyl or hydrogen,
- $R_6$ is trialkylsilyl, hydrogen or a negative charge, and
- $A_1^{\ominus}$ is an anion, with the condition that n is zero when $R_6$ is a negative charge, and n is one when $R_6$ is trialkylsilyl or hydrogen, which comprises the steps of a-i) reacting a compound of formula

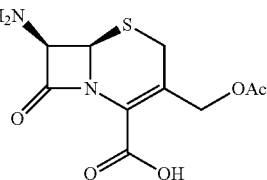

III with a silylating agent, optionally in presence of a catalyst, and
with iodotrialkylsilane, a-ii) providing a compound of formula

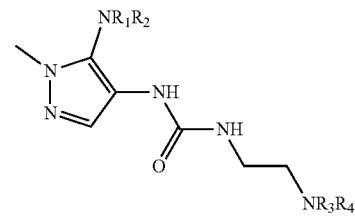

IV wherein
$R_1$-$R_4$ are as defined above, and
optionally reacting this compound of formula IV with a silylating agent, a-iii) reacting the products of steps a-i) and a-ii), a-iv) and optionally desilylating the product of step a-iii) to produce the compound of formula II b) preparing a compound of formula

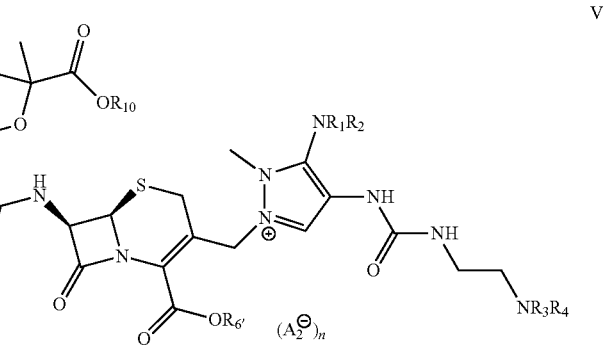

V wherein
$R_1$-$R_4$ and $R_{6'}$ are as defined above,
$R_7$ is hydrogen or an amino protecting group,
$R_{10}$ is an ester protecting group, and
$A_2^{\ominus}$ is an anion, with the condition that n is zero when $R_{6'}$ is a negative charge, and n is one when $R_{6'}$ is hydrogen, which comprises the step of
reacting the compound of formula II with a compound of formula

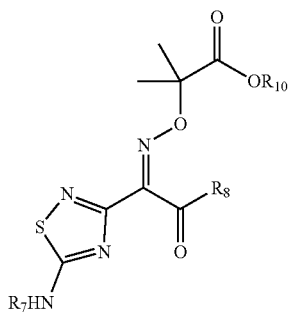

wherein R$_7$ and R$_{10}$ are as defined above,

R$_8$ is Cl or SR$_9$, wherein R$_9$ is C$_1$-C$_6$ straight or branched alkyl, C$_3$-C$_6$ cycloalkyl, or a substituted or unsubstituted mono- or bicyclic aryl or heteroaryl ring system of 5 to 12 atoms and where each monocyclic ring contains 0 to 3 hetero atoms, and each bicyclic ring contains 0 to 4 hetero atoms selected from N, O and S, and c) removing any protecting groups from the compound of formula V to produce a compound of formula I, d) if in the compound of formula I produced in step c) R$_{6'}$ is a negative charge and n is zero optionally treating the compound of formula I produced in step c) with an acid to produce a compound of formula I, wherein R$_{6'}$ is hydrogen and n is one, e) optionally exchanging the anion by a different anion in the compound of formula I produced in step d) or in the compound of formula I produced in step c) if R$_{6'}$ is hydrogen and n is one.

2. The method of claim 1, comprising the step a-ii) reacting a compound of formula

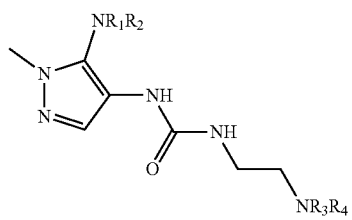

wherein

R$_1$-R$_4$ are as defined in claim 1, with a silylating agent.

3. The method of claim 1, wherein step a-iii) is carried out in the presence of a metal catalyst.

4. The method of claim 1, wherein in each of the compounds of formulae II, IV, and V, at least one of R$_1$ and R$_2$ is triphenylmethyl, trialkylsilyl, tert-butyldimethylsilyl or triisopropylsilyl, or tert-butyldiphenylsilyl or R$_1$ and R$_2$ are both benzyl or both allyl, at least one of R$_3$ and R$_4$ is tert-butyloxycarbonyl, triphenylmethyl, benzoyloxycarbonyl (Cbz), allyloxycarbonyl (Aloc), 9-fluorenylmethoxycarbonyl (Fmoc), methoxycarbonyl, ethoxycarbonyl, 2-(trimethylsilyl)ethoxycarbonyl (Teoc), 2,2,2-trichlorethoxycarbonyl (Troc) or part of a triazinanone or trimethylsilyl or R$_3$ and R$_4$ are both benzyl, allyl, or (p-methoxybenzyl), R$_5$ and R$_6$ are trimethylsilyl, R$_7$ is hydrogen, R$_8$ is Cl or

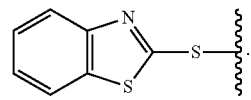 [SMILES: *Sc1nc2ccccc2s1]

5. The method of claim 1, wherein steps a-i) and a-ii) are independently conducted in one or a combination of two or more solvents selected from the group consisting of N-methyl-2-pyrrolidone, 1,3-dimethyl-3,4,5,6-tetrahydro-2(1H)-pyrimidinone, dimethylacetamide, 1,3-dimethyl-2-imidazolidinone, dimethylformamide, dimethyl sulfoxide or methylene chloride.

6. The method of claim 1, wherein the compound of formula II is not isolated from the reaction mixture of step a) before it is reacted with the compound of formula VI in step b).

7. The method of claim 1, wherein one or more acids are used in step c) for removing any protecting groups from the compound of formula V to produce a compound of formula I, wherein R$_{6'}$ is hydrogen and n is one.

8. The method of claim 1, wherein R$_1$ is triphenylmethyl and R$_2$ is hydrogen and step c) comprises a step c1) wherein all triphenylmethyl groups are selectively removed from the compound of formula V

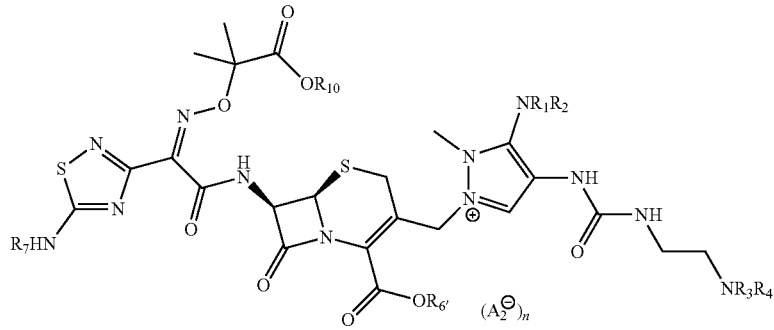

to produce a compound of formula VII

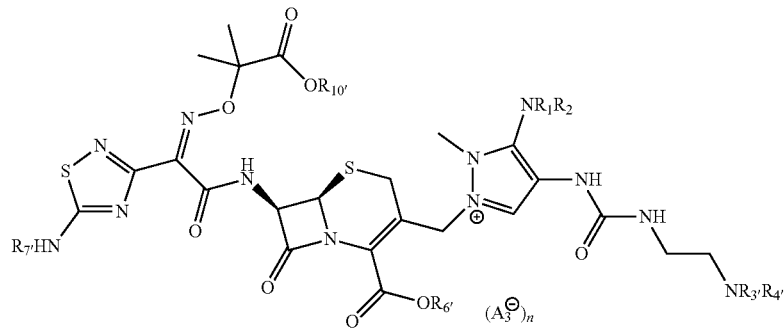

VII wherein
R$_{3'}$, R$_{4'}$, R$_{6'}$, R$_{7'}$ and R$_{10'}$ are defined as R$_3$, R$_4$, R$_{6'}$, R$_7$ and R$_{10}$ in claim 1, respectively with the exception that R$_{3'}$, R$_{4'}$, R$_{7'}$ and R$_{10'}$ are not triphenylmethyl and if R$_3$ and/or R$_4$ and/or R$_7$ and/or R$_{10}$ are triphenylmethyl in the compound of formula V R$_{3'}$ and/or R$_{4'}$ and/or R$_{7'}$ and/or R$_{10'}$ are hydrogen in the compound of formula VII, respectively, and A$_3^{\ominus}$ is an anion, with the condition that n is zero when R$_{6'}$ is a negative charge, and n is one when R$_{6'}$ is hydrogen.

9. The method of claim 8, wherein formic acid in ethanol is used in step c1) for selectively removing all triphenylmethyl groups, from the compound of formula V to form a compound of formula VII, wherein R$_{6'}$ is hydrogen, n is one and A$_3^{\ominus}$ is formate.

10. The method of claim 8, wherein the reaction mixture of step c1) is subjected to an aqueous workup and insoluble precipitate is removed before any remaining protective groups of the compound of formula VII are removed in a step c2) to produce a compound of formula I.

11. The method of claim 1, wherein in step c) H$_2$SO$_4$ is used to produce a compound of formula I, wherein R$_{6'}$ is hydrogen, n is one and A$^{\ominus}$ is HSO$_4^-$ and a solvent is used, which is selected from one or a combination of two or more solvents of the group consisting of 2,2,2,-trifluoroethanol, methyl isobutyl ketone, 2-ethoxyethanol, acetic acid, methyl ethyl ketone, dimethylcarbonate and acetonitrile.

12. A method for preparing a compound of formula I as defined in claim 1 from a compound of formula V

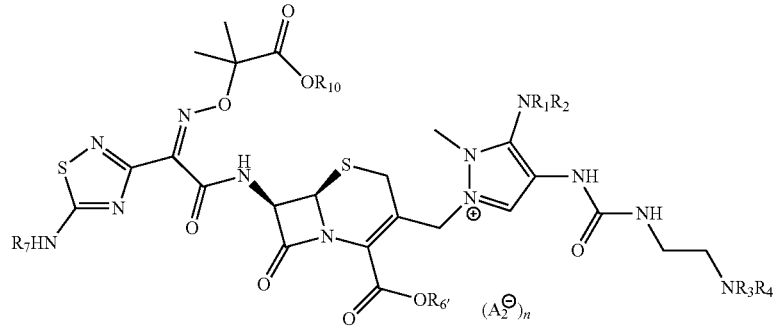

V wherein
R$_1$, R$_2$, R$_3$ and R$_4$ are independently an amino protecting group or hydrogen with the condition that R$_4$ is not hydrogen if R$_3$ is hydrogen, or R$_1$ and R$_2$, and/or R$_3$ and R$_4$ are bound together by a cyclic amino protecting group,
R$_{6'}$ is hydrogen or a negative charge, and
R$_7$ is hydrogen or an amino protecting group,
R$_{10}$ is an ester protecting group, and
A$_2^\ominus$ is an anion, with the condition that n is zero when R$_{6'}$ is a negative charge, and n is one when R$_{6'}$ is hydrogen,
or from a compound of formula VII

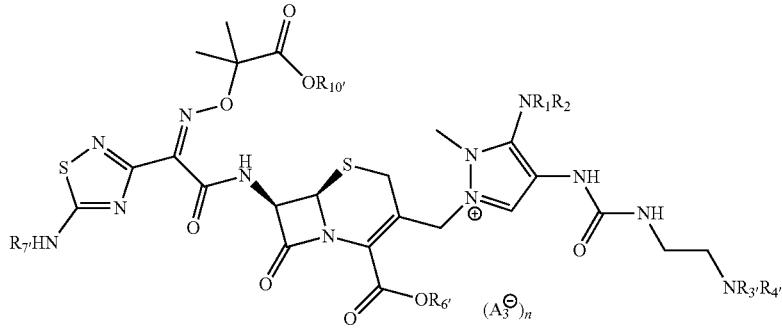

VII wherein
R$_{3'}$, R$_{4'}$, R$_{6'}$, R$_{7'}$ and R$_{10'}$ are defined as R$_3$, R$_4$, R$_{6'}$, R$_7$ and R$_{10}$ in claim 1, respectively with the exception that R$_{3'}$, R$_{4'}$, R$_{7'}$ and R$_{10'}$ are not triphenylmethyl and if R$_3$ and/or R$_4$ and/or R$_7$ and/or R$_{10}$ are triphenylmethyl in the compound of formula V R$_{3'}$ and/or R$_{4'}$ and/or R$_{7'}$ and/or R$_{10'}$ are hydrogen in the compound of formula VII, respectively, and
A$_3^\ominus$ is an anion, with the condition that n is zero when R$_{6'}$ is a negative charge, and n is one when R$_{6'}$ is hydrogen.

13. A method for preparing a compound of formula VII as defined in claim 8 from a compound of formula V

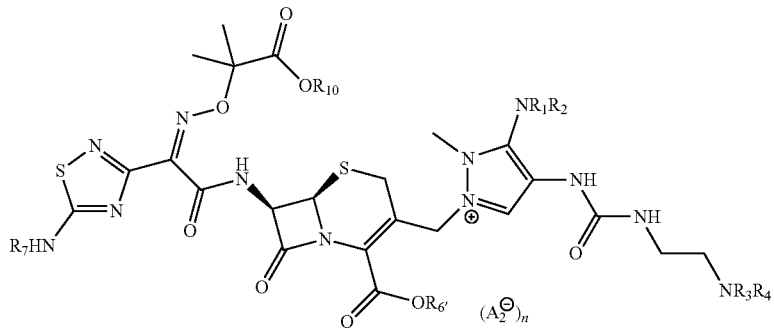

V wherein
R$_1$, R$_2$, R$_3$ and R$_4$ are independently an amino protecting group or hydrogen with the condition that R$_4$ is not hydrogen if R$_3$ is hydrogen, or R$_1$ and R$_2$, and/or R$_3$ and R$_4$ are bound together by a cyclic amino protecting group,
R$_{6'}$ is hydrogen or a negative charge, and
R$_7$ is hydrogen or an amino protecting group,
R$_{10}$ is an ester protecting group, and
A$_2^\ominus$ is an anion, with the condition that n is zero when R$_{6'}$ is a negative charge, and n is one when R$_{6'}$ is hydrogen, comprising a step c1) as defined in claim 8.

14. The method of claim 10, wherein in step c2) H$_2$SO$_4$ is used to produce a compound of formula I, wherein R$_{6'}$ is hydrogen, n is one and A$^\ominus$ is HSO$_4^-$ and a solvent is used, which is selected from one or a combination of two or more solvents of the group consisting of 2,2,2,-trifluoroethanol, methyl isobutyl ketone, 2-ethoxyethanol, acetic acid, methyl ethyl ketone, dimethylcarbonate and acetonitrile.

* * * * *